United States Patent [19]

Albarella et al.

[11] Patent Number: 5,089,420
[45] Date of Patent: Feb. 18, 1992

[54] COMPOSITION, DEVICE AND METHOD OF ASSAYING FOR A PEROXIDATIVELY ACTIVE SUBSTANCE UTILIZING AMINE BORATE COMPOUNDS

[75] Inventors: James P. Albarella; Michael J. Pugia, both of Granger, Ind.

[73] Assignee: Miles Inc., Elkhart, Ind.

[21] Appl. No.: 472,282

[22] Filed: Jan. 30, 1990

[51] Int. Cl.$^5$ .................. G01N 21/78; G01N 33/72
[52] U.S. Cl. ........................... 436/66; 422/56; 435/28; 435/805; 436/169; 436/175; 436/904
[58] Field of Search ............ 436/66, 73, 169, 175, 436/904; 422/56-58; 435/28, 805

[56] References Cited

U.S. PATENT DOCUMENTS 3,853,471 12/1974 Rittersdorf et al. .................. 436/66
4,071,318 1/1978 Lam .................................. 436/66 X
4,071,321 1/1978 Lam .................................. 436/66

OTHER PUBLICATIONS

Steinberg et al., JACS, vol. 82, No. 4, pp. 853-859, 02/1960.

Primary Examiner—Robert J. Hill, Jr.
Attorney, Agent, or Firm—Roger N. Coe

[57] ABSTRACT

A new and improved test device and method of determining the presence or concentration of a peroxidatively active substance, such as hemoglobin, in a test sample are disclosed. The test device includes a test pad comprising a suitable carrier matrix incorporating an indicator reagent composition capable of interacting with a peroxidatively active substance to produce a detectable or measurable response. In addition, a new and improved indicator reagent composition, comprising an indicator dye, such as a redox indicator, like a benzidine indicator; a hydroperoxide; an amine borate compound having the general structural formula:

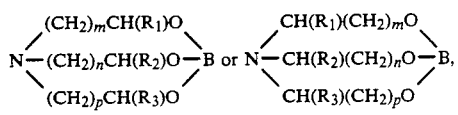

wherein $R_1$, $R_2$, and $R_3$ are, independently, methyl groups or ethyl groups, and m, n and p are numerals ranging from one to about three; a buffer, is incorporated into a suitable carrier matrix to provide a more accurate and trustworthy assay of a test sample for a peroxidatively active substance. The improved method and composition are especially useful in the assay of urine for occult blood.

50 Claims, No Drawings

COMPOSITION, DEVICE AND METHOD OF ASSAYING FOR A PEROXIDATIVELY ACTIVE SUBSTANCE UTILIZING AMINE BORATE COMPOUNDS

FIELD OF THE INVENTION

The present invention relates to a composition, device and method of determining the presence or concentration of a peroxidatively active substance in a test sample. More particularly, the present invention relates to a new and improved method of assaying a liquid test sample, such as urine, for a peroxidatively active substance, like occult blood, by utilizing a more stable indicator reagent composition. The indicator reagent composition undergoes a detectable or a measurable response upon contact with a test sample containing a peroxidatively active substance. The indicator reagent composition of the present invention provides a more accurate and sensitive assay for a peroxidatively active substance by effectively stabilizing the indicator dye present in the indicator reagent composition prior to contact between the indicator reagent composition and the test sample. Accordingly, the improved sensitivity achieved by the indicator reagent composition of the present invention provides an improved method of assaying a test sample for a low concentration of a peroxidatively active substance, such as assaying urine for occult blood.

BACKGROUND OF THE INVENTION AND PRIOR ART

Peroxidase is an enzyme that catalyzes the oxidation of various compounds, such as phenols and amines, by peroxides. In addition, particular compounds have been termed pseudoperoxidases because these compounds behave in a manner similar to the peroxidase enzyme. Accordingly, pseudoperoxides liberate oxygen from hydroperoxides and transfer the oxygen to certain acceptor compounds. Therefore, in general, the pseudoperoxidases are enzyme-like in that they catalyze, or otherwise participate in, reactions between peroxides and oxidizable compounds. The pseudoperoxidases also are termed peroxidatively active substances, and include hemoglobin and its derivatives.

For example, in the assay of urine for glucose, glucose oxidase, in the presence of oxygen, first converts the glucose in the urine to gluconic acid and hydrogen peroxide. Then, the peroxidase enzyme, also present in the assay, catalyzes the interaction between the hydrogen peroxide and an oxidizable dye compound, like o-tolidine. The dye compound, usually essentially colorless in its reduced state, undergoes a color transition upon oxidation, such as to a blue color for o-tolidine, by the peroxidase-catalyzed interaction with hydrogen peroxide. The degree and intensity of the color transition are directly proportional to the amount of hydrogen peroxide generated by the glucose conversion. Then, the amount of hydrogen peroxide generated by the glucose conversion is correlated to the original concentration of glucose in the urine sample.

Similarly, a peroxidatively active substance, like hemoglobin and its derivatives, catalyzes the interaction between a hydroperoxide and an oxidizable dye. In such interactions, the peroxidatively active substance imitates the peroxidase enzyme, and catalyzes or otherwise participates in an interaction between the oxidizable dye and the hydroperoxide. The oxygen liberated from a hydroperoxide by a peroxidatively active substance is transferred to an oxidizable dye. The resulting interaction provides a detectable response, such as a color transition, wherein the intensity of the response is indicative of the presence or the concentration of the peroxidatively active substance.

Assays for a peroxidatively active substance are based upon the above-described chromogenic interaction, wherein the degree and intensity of the color transition of the indicator dye are correlated to the concentration of the peroxidatively active substance in the test sample. Assays for a peroxidatively active substance are particularly useful in detecting and measuring low concentrations of blood, often termed "occult" blood, in body fluid samples such as urine, feces or gastrointestinal contents. Although occult blood in urine, feces or vomit usually is not visible to the naked eye, the detection of occult blood is important in the diagnosis of hemorrhages in the stomach, intestines and urinary tract. The hemorrhages are caused, for example, by tumors, ulcers or inflammations of the organ in question. Presently, most methods of determining the presence of occult blood in a test sample are based upon the pseudoperoxidase activity of hemoglobin or myoglobin.

Although protein in urine is the most important indicator of renal dysfunction, the presence of blood in urine also is an indication of damage to the kidney or urinary tract. Normally, detectable amounts of occult blood are not present in urine, even with very sensitive chemical methods. Blood in the urine can appear as intact red blood cells or as free hemoglobin. Usually the presence of free hemoglobin indicates that the blood cells have ruptured either because of a traumatic passage through the kidney and urinary tract to the bladder, or because the blood cells have been exposed to dilute urine in the bladder that caused the cells to hemolyze.

More particularly, the presence of blood in urine or feces is a symptom of a variety of abnormal conditions, including cancer. The presence of blood in urine, as indicated by a positive test for occult blood, often indicates bleeding in the urinary tract. Free hemoglobin is present in the urine because of renal disorders, infectious diseases, neoplasms, or traumas affecting part of the urinary tract. Free hemoglobin in the urine also can indicate a transfusion reaction, hemolytic anemia, or paroxysmal hemoglobinuria, or can appear from various poisonings or following severe burns. In addition, a positive chemical test for hemoglobin, without the presence of red cells, can indicate myoglobinuria as a result of traumatic muscle injury.

Hemoglobinuria is defined as the presence of free hemoglobin in the urine without red blood cells. In contrast, hematuria is defined as the presence of intact red blood cells in urine. Hematuria is indicative of a specific defect in the microscopic functional unit (the nephron) of the kidney, and is indicative of bleeding in the kidney, the ureter, the bladder or the urethra. The free hemoglobin in the plasma is excreted by the kidney into the urine. In some situations, hemolysis of the red blood cells occurs after the cells have entered the urine. Most urine samples containing red blood cells also contain some hemolyzed occult blood. Presently, the differentiation of trace amounts of blood as cells versus free hemoglobin is of little significance.

Myoglobin, the red respiratory pigment of muscle tissue, is another peroxidatively active substance. Myoglobin is very similar to hemoglobin in its composition and chemical reactions. Myoglobin can be liberated from muscle cells by certain types of injury, and in such cases the myoglobin will circulate in the plasma, and then be excreted in the urine. In addition, certain genetic muscle disorders can cause the muscles to lose myoglobin that subsequently appears in the urine. Myoglobin also is found in the urine after a cardiac infarct.

Hematuria, hemoglobinuria or myoglobinuria depends upon the precise nature of the clinical and pathological disorder and upon the severity of the specific disease or injury. In addition, other peroxidatively active substances also are present in leukocytes and bacteria. Overall, the detection of a peroxidatively active substance is especially important in the diagnosis of diseases and infections of the kidneys and urinary tract.

Therefore, accurate and thorough assays of urine and other test samples for peroxidatively active substances must be available for both laboratory and home use. The assays must permit the detection and measurement of the peroxidatively active substance such that a correct diagnosis can be made and correct medical treatment implemented, monitored and maintained. In addition, it would be advantageous if the assay method could be utilized in a dip-and-read format for the easy and economical, qualitative or quantitative determination of a peroxidatively active substance in urine or other rest samples.

Furthermore, any method of assaying for a peroxidatively active substance in urine or other test sample must yield accurate, trustworthy and reproducible results by utilizing an indicator reagent composition that undergoes a color transition as a result of an interaction with a peroxidatively active substance, and not as a result of a competing chemical or physical interaction, such as a preferential interaction with a test sample component other than a peroxidatively active substance or a color transition occurring due to the instability of the indicator reagent composition. Moreover, it would be advantageous if the assay method for a peroxidatively active substance is suitable for use in dry phase reagent strips for the rapid, economical and accurate determination of a peroxidatively active substance in urine or other test sample. Additionally, the method and composition utilized in the assay for a peroxidatively active substance should not adversely affect or interfere with the other test reagent pads that are present on multideterminant reagent strips.

Therefore, in order to determine if an individual is excreting a peroxidatively active substance, and in order to monitor the course of medical treatment to determine the effectiveness of the treatment, simple, accurate and inexpensive detection assays for a peroxidatively active substance, like occult blood, have been developed. Furthermore, of the several different assay methods developed for the detection or measurement of occult blood in urine, the methods based on dip-and-read dry phase test strips have proven especially useful because dry phase test strip methods are readily automated and provide reproducible and accurate results.

Some tests strips used in assays for peroxidatively active substances have a single test area consisting of a small square pad of a suitable carrier matrix impregnated with an indicator reagent composition comprising an indicator dye, such as a benzidine dye; a hydroperoxide; and a buffer. Other test strips are multideterminant reagent strips that include one test area for the assay of a peroxidatively active substance as described above, and further include several additional test areas on the same strip to permit the simultaneous assay of other urinary constituents. For both types of colorimetric test strips, the assay for a peroxidatively active substance in urine is performed simply by dipping the colorimetric test strip into a well mixed, uncentrifuged urine sample, then comparing the resulting color of the test area of the test strip to a standardized color chart provided on the colorimetric test strip bottle. Occult blood tests usually are included on multideterminant reagent strips to screen urine samples during routine physical examinations because it is important to detect a bleeding condition early.

The test strip method is the simplest and most direct assay for the presence of blood in urine. The test area is impregnated with an oxidizable indicator dye, like 3,3',5,5'-tetramethylbenzidine, and a buffered hydroperoxide. The test area becomes a green to dark blue color when hemoglobin present in the urine sample catalyzes the oxidation reaction of tetramethylbenzidine by the hydroperoxide. The development of green spots on the tests area indicates intact, nonhemolyzed erythrocytes. In accordance with the above-described method, an individual can readily determine, visually, the concentration of a peroxidatively active substance in a urine sample. The color of the test strip is compared with a color chart approximately one minute after the test strip is dipped into the urine. The color blocks on the color chart indicate negative, nonhemolyzed trace, hemolyzed trace, small (1+), moderate (2+), and large (3+) amounts of blood. The color chart ranges from orange through green to blue. The assay usually is capable of detecting from about 0.015 to about 0.06 mg/dL (milligrams per deciliter) of free hemoglobin or from about 5 to about 20 intact red blood cells per microliter.

In addition, ascorbate ion, when present, seriously interferes in the above-described assay method for a peroxidatively active compound. It has been found that including certain metal ion complexes in the indicator reagent composition essentially eliminate the ascorbate interference problem. However, in general, the metal ion complexes also demonstrate peroxidase activity, and behave similarly to peroxidase or the pseudoperoxidases to catalyze the color-forming reaction between a hydroperoxide and a oxidizable dye. Accordingly, although the metal ion complexes eliminate ascorbate interference, the metal ion complexes also can produce false positive assays because the metal ion complexes can catalyze oxidation of the oxidizable dye by the hydroperoxide, thereby producing a color change in the device even though a peroxidatively active substance is not present in the test sample.

Investigators have found that particular ferric ion complexes substantially reduced the false positive assay results attributed to most metal ion complexes used to eliminate ascorbate interference. However, although the ferric ion complexes effectively eliminated ascorbate interferences and demonstrated a substantially reduced peroxidative activity, the indicator reagent composition had to be buffered to a pH value that does not provide the optimum color transition.

Therefore, it would be extremely advantageous to provide a simple, accurate and trustworthy method of assaying urine for low levels of a peroxidatively active substance. Present day test strips for a peroxidatively active substance incorporate an indicator reagent composition that includes an amine borate stabilizer. However, the amine borates used in the prior art have the disadvantage of hydrolyzing upon exposure to environmental humidity, resulting in an increased pH of the indicator reagent composition. Consequently, the present day indicator reagent compositions, also including a metal ion complex for ascorbate resistance and buffered at a pH that does not provide the most spectacular color transition, increase in pH due to hydrolysis of the amine borates. Therefore, the sensitivity of the assay for a peroxidatively active substance is decreased. Surprisingly and unexpectedly, the method of the present invention essentially eliminates an increase in pH of the indicator reagent composition after exposure to humid conditions by including a hydrolysis-resistant amine borate in the indicator reagent composition. Therefore, the problem of decreased assay sensitivity is solved, even in the presence of a compound, like a metal ion complex, to eliminate ascorbate interference.

Accordingly, a quantitative urine assay for a peroxidatively active substance can be performed by laboratory personnel to afford immediate and trustworthy test results by providing a more accurate assay method in an easy-to-use form, such as a dip-and-read test strip. In addition, the test strip method can be performed by the patient at home to more precisely monitor the level of a peroxidatively active substance in urine and/or the success of the medical treatment the patient is undergoing.

As will be described more fully hereinafter, the method of the present invention allows the fast, accurate and trustworthy assay for a peroxidatively active substance by utilizing a test strip that includes a test pad comprising a suitable carrier matrix impregnated with an indicator reagent composition of the present invention. The indicator reagent composition comprises an indictor dye; a hydroperoxide; a bicyclic amine borate compound that resists hydrolysis upon exposure to humid conditions; and a buffer. The indicator reagent composition is sensitive to low concentrations of a peroxidatively active substance; stabilizes the indicator dye and thereby essentially eliminates a premature interaction between the indicator dye and a hydroperoxide; and, surprisingly and unexpectedly, essentially eliminates an increase in the pH of the test strip upon exposure to humid conditions. Accordingly, the improved stability of the indicator reagent composition enhances the sensitivity of the assay, thereby providing a more accurate and trustworthy assay for a peroxidatively active substance.

Prior to the present invention, no known method of assaying urine or other test samples for peroxidatively active substances included an indicator reagent composition comprising an indicator dye; a hydroperoxide; a buffer; and a hydrolysis-resistant amine borate that stabilizes the indicator dye of the indicator reagent composition. Although a dry phase test strip including an oxidizable indicator dye, such as o-tolidine or 3,3=,5,5'-tetramethylbenzidine; a buffer; and a hydroperoxide has been used previously, dry phase test strips incorporating these three compounds demonstrated a tendency to undergo a color transition due to a premature interaction between the hydroperoxide and the indicator dye. Accordingly, such a false positive assay decreased the utility and the sensitivity of the test strip to the peroxidatively active substance in the test sample. The indicator reagent composition of the present invention essentially eliminates a premature interaction between the indicator dye and the hydroperoxide. Consequently, the improved stability of the indicator reagent composition increases the sensitivity of the assay such that an accurate and trustworthy assay for a peroxidatively active substance is achieved.

The prior art contains numerous references on the wet phase chemistry and the dry phase chemistry utilized in assaying urine for a peroxidatively active substance. For example, investigators developed wet chemistry assay procedures and dry phase test strip devices for peroxidatively active substances that rely on the enzyme-like catalysis of the peroxidative oxidation of indicator dyes. An example of a wet chemistry assay for a peroxidatively active substance is presented in R. M. Henry, et al., *Clinical Chemistry Principles and Techniques*, 2nd ed., Harper and Row, pp. 1124-1125 (1974). This wet phase assay procedure employs glacial acetic acid as a buffer, diphenylamine as an indicator dye and hydrogen peroxide. Although such wet phase assays are analytically useful, they nevertheless possess severe disadvantages, including poor reagent stability and inadequate analyte sensitivity. For instance, the reagent solutions used in the wet phase assays rapidly decline in stability, and consequently in sensitivity. Therefore, fresh reagent solutions must be prepared after a few days of storage. The continuous preparation of fresh reagent solutions is time-consuming and uneconomical because costly reagents are wasted.

The preferred method of assaying for a peroxidatively active substance utilizes a dry phase test strip device. A typical dry phase test strip is commercially available from the Diagnostics Division of Miles, Inc. under the trademark HEMASTIX®. The test strip comprises a test pad, including a porous carrier matrix, such as a paper matrix, impregnated with a buffered mixture of an organic hydroperoxide and an indicator dye, affixed to a plastic strip or handle. The test pad is immersed in a test sample containing hemoglobin, myoglobin, erythrocytes or another peroxidatively active substance, and the test pad develops a blue color. The intensity of the blue color is proportional to the concentration of the peroxidatively active substance in the test sample. By comparing the color developed in the test pad to a standardized color chart, the analyst can determine, quantitatively, the amount of a peroxidatively active substance present in the test sample.

In general, dry phase test strips are more advantageous than the wet phase assays because the test strip format is easier to use, requiring neither the continual preparation of reagents nor the attendant apparatus. In addition, reagent stability is greater in the dry phase test strip, thereby resulting in improved assay accuracy, sensitivity and economy. Notwithstanding that present day test strips for determining peroxidatively active substances are substantially more stable and more sensitive than wet phase assays, present day strips need improvement in the areas of stability and sensitivity. Therefore, it would be a significant advance in the art of diagnostic assays if test strips were even more stable during storage and even more sensitive to peroxidatively active substances. It was towards achieving these improvements that the investigations resulting in the composition, device and method of the present invention were directed.

Several attempts at achieving the above-mentioned goals of increased stability and sensitivity are found in the prior art. For example, in *Chemical Abstracts*, Vol. 85, p. 186 (1976), a two-dip method of preparing a dry phase test strip containing o-tolidine and phenylisopropyl hydroperoxide is described. In this method, filter paper strips impregnated with ethyl cellulose were dipped into an ethanolic solution comprising an indicator, o-tolidine hydrochloride; polyvinyl pyrrolidone; a surfactant; and sufficient citrate buffer to provide a pH of 3.7. The impregnated filter paper then was dried, and subsequently was dipped into an ethanol-toluene solution containing 1,4-diazobicyclo[2.2.2]octane, phenylisopropyl hydroperoxide and polyvinylpyrrolidone. The investigators desired to stabilize the hydroperoxide with the diazobicyclooctane compound and the polyvinylpyrrolidone, and therefore eliminate a premature interaction with the indicator dye.

Lam, in U.S. Pat. No. 4,071,318, disclosed a composition comprising a hydroperoxide, an indicator dye, and a bicyclic amine borate that is useful in the assay for a peroxidatively active substance. Lam theorized that the bicyclic amine borate complexed with the hydroperoxide, thereby inhibiting the hydroperoxide from interacting with the indictor dye during storage. Therefore, the improved stability of the composition provided more accurate assays for a peroxidatively active substance by reducing the premature oxidation of the indicator dye. However, the amine borates utilized by Lam, such as triethanolamine borate and tri(n-propanol)amine borate were found to hydrolyze upon exposure to environmental humidity and cause a rise in the pH of the indicator reagent composition incorporated in the test pad. The resulting increase in pH caused a decrease in the sensitivity of the assay for a peroxidatively active substance.

H. Steinberg and D. L. Hunter, in the publications, "Preparation and Rate of Hydrolysis of Boric Acid Esters", *Ind. and Eng. Chem.*, 49,2, pp. 174-181 (1974) and "The Hydrolysis of Triisopropanolamine Borate", *J. Am. Chem. Soc.*, 82, pp. 853-859 (1960), disclosed that bicyclic amine borates having pendant methyl groups, like triisopropanolamine borate, hydrolyze substantially more slowly than bicyclic amine borates that do not include pendant methyl groups, like triethanolamine borate. Steinberg et al theorized that the increased stability is attributable to the steric effects introduced by the pendant methyl groups in triisopropanolamine borate. However, the publications of Steinberg et al neither teach nor suggest that sterically-hindered bicyclic amine borates are useful in assays for peroxidatively active substances.

Adams et al, in U.S. Pat. No. 3,252,762, disclosed physically-encapsulating an organic hydroperoxide within a colloidal material, such as gelatin, to stabilize the test strip. Accordingly, when an aqueous test sample contacts the test strip, the gelatin capsules dissolve, thereby freeing the hydroperoxide for an interaction with an indicator dye that is mediated by a peroxidatively active substance. However, the encapsulation process of Adams is time-consuming and requires relatively expensive apparatus and excessive manipulative steps. Each of these prior art disclosures was directed at stabilizing the reagents incorporated into the test pad of the test strip such that the potentially incompatible reagent ingredients, i.e., the hydroperoxide and the indicator dye, would not prematurely interact, and thereby provide a false positive assay or render the test strip less sensitive to a peroxidatively active substance.

Another test strip and method are disclosed in U.S. Pat. No. 3,853,471 to Rittersdorf et al. Rittersdorf described the use of phosphoric acid amides or phosphonic acid amides to stabilize test strips used to assay for peroxidatively active substances. The phosphoric or phosphonic acid amides disclosed by Rittersdorf sufficiently stabilized the hydroperoxide and indicator dye such that the test strips did not become discolored due to a premature interaction between the hydroperoxide and the indicator dye.

Ku, in U.S. Pat. No. 3,411,887, described the elimination of ascorbate interference with reagent compositions that rely on enzymatic oxidizing substances, such as glucose oxidase, by using an ascorbate "trapping system". The "trapping system" utilizes a heavy metal ion that has an oxidation-reduction reduction potential falling between a redox indicator dye and ascorbate. Suitable heavy metal compounds cited as examples include cobalt, iron, mercury and nickel. In addition to the disclosure of Ku, the prior art also discloses that metal ions, such as Co(III), are actually pseudoperoxidases. For example, *The Merck Index*, 9th ed., p. 311 (1976) discloses the Co(III) acetate is used commercially to catalytically decompose cumene hydroperoxide. In addition, a series of Co(III) complexes to catalytically decompose peroxides are reported by K. Lohs, *Monatsber. Deut. Adad. Wiss. Berlin*, 8, pp. 657-659 (1966).

U.S. Pat. No. 4,587,220, to Mayambala-Mwanika et al., disclosed the use of a chelated ferric ion to eliminate ascorbic acid and ascorbate ion interference in an assay for a peroxidatively active substance. Mayambala-Mwanika disclosed that a ferric chelate, like the ferric chelate of N-(2-hydroxyethyl)ethylenediaminetriacetic acid (Fe—HEDTA), eliminated ascorbate interference and did not produce a false positive test for the peroxidatively active compound. In accordance with the method of Mayambala-Mwanika, a two-step method of preparing the test device provided an ascorbate-resistant test pad that demonstrated sufficient stability to resist a false positive assay result during storage.

In contrast to the prior art, and in contrast to the presently available commercial test strips, the composition of the present invention has increased stability and therefore imparts increased sensitivity to a test strip used in the detection and measurement of a peroxidatively active substance in a test sample. The method of the present invention utilizes an indicator reagent composition that stabilizes the indicator dye, and therefore essentially eliminates indicator dye interaction with the hydroperoxide until the indicator dye contacts a test sample containing a peroxidatively active substance.

Surprisingly, the method and composition of the present invention essentially eliminate color formation, or other detectable responses, attributable to a premature indicator dye oxidation by the hydroperoxide. Hence, in accordance with the method of the present invention, new and unexpected results are achieved in the dry phase test strip assay of urine and other test samples for a peroxidatively active substance by utilizing a stable indicator reagent composition that includes a hydrolysis-resistant amine borate having pendate methyl groups and/or ethyl groups.

SUMMARY OF THE INVENTION

In brief, the present invention is directed to a new and improved composition, test device and method of determining the presence or concentration of a component in a test sample. The device includes a test pad comprising a suitable carrier matrix incorporating an indicator reagent composition capable of interacting with a test sample component to produce a detectable response. For home use, the indicator reagent composition produces a visually detectable response. For laboratory use, the indicator reagent composition produces a response that is detectable visually or by instrument. The carrier matrix of the test pad comprises a bibulous material, such as filter paper; a nonbibulous material, such as a strip, layer or membrane of a polymerized material; or a combination thereof. An indicator reagent composition is homogeneously incorporated into the carrier matrix, and the carrier matrix then holds the indicator reagent composition homogeneously throughout the carrier matrix while maintaining carrier matrix penetrability by the predetermined component of the test sample.

More particularly, the present invention is directed to a method of assaying urine or other test samples for a peroxidatively active substance by utilizing a new and improved indicator reagent composition. It has been demonstrated that an indicator reagent composition comprising: (a) an indicator dye, like a redox indicator, capable of undergoing a color transition in response to a peroxidatively active substance; (b) a hydroperoxide; (c) a buffer; and (d) amine borate compound having the general structural formula:

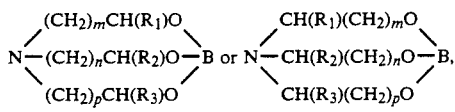

wherein $R_1$, $R_2$, and $R_3$ are, independently, methyl groups or ethyl groups, and m, n and p are numerals ranging from one to about three, has improved stability, and therefore increased sensitivity to a peroxidatively active substance.

The bicyclic amine borate included in the indicator reagent composition effectively resists hydrolysis upon exposure to environmental humidity. Accordingly, the hydrolysis-resistant amine borate sufficiently stabilizes the indicator dye until contact between the test pad incorporating the indicator reagent composition and the test sample allows the peroxidatively active substance to mediate the interaction between the indicator dye and the hydroperoxide. In addition, the hydrolysis-resistant bicyclic amine borate included in the indicator reagent composition does not yield alkaline hydrolysis products that increase the pH of the indicator reagent composition included in the test strip, that in turn results in a less spectacular color transition and a less sensitive assay for a peroxidatively active substance.

In accordance with an important feature of the present invention, a more accurate and reliable qualitative or quantitative determination of a peroxidatively active substance in a test sample is accomplished because the indicator reagent composition effectively resists the color-forming oxidation of the indicator dye by the hydroperoxide prior to contact between the indicator reagent composition and a test sample including a peroxidatively active substance. By utilizing the indicator reagent composition of the present invention in clinical test methods, the qualitative or quantitative assay for a peroxidatively active substance, such as hemoglobin, in urine or other test samples is more accurate because the indicator reagent composition does not yield false positive assays due to premature oxidation of the indicator dye.

Therefore, it is an object of the present invention to provide a new and improved method and test device for determining the relative concentration of a chemical compound in a liquid test sample.

Another object of the present invention is to provide a simple, trustworthy, accurate and reproducible method of assaying urine and other test samples for a peroxidatively active substance.

Another object of the present invention is to provide a method of assaying urine or other liquid test samples for a peroxidatively active substance utilizing a stable indicator reagent composition that provides increased sensitivity to the peroxidatively active substance.

Yet another object of the present invention is to provide a method of assaying biological test samples that is sensitive to low concentrations of a peroxidatively active substance and that substantially eliminates false positive assays.

Another object of the present invention is to provide a method of assaying urine or other liquid test samples for occult blood that is sufficiently sensitive to detect occult blood in concentrations as low as about one part of occult blood per one trillion parts of test sample.

Another object of the present invention is to provide a method of assaying urine or other test liquids for a peroxidatively active substance utilizing an indicator reagent composition comprising an indicator dye, a hydroperoxide, a buffer and a bicyclic amine borate including pendant methyl groups or ethyl groups, wherein the premature oxidation of the indicator dye present in the indicator reagent composition by the hydroperoxide is essentially eliminated.

Another object of the present invention is to provide a method of assaying urine or other test samples by utilizing an indicator reagent composition that effectively stabilizes the indicator dye, and therefore essentially eliminates oxidation of the indicator dye prior to contact with the test sample; and that, upon contact with a test sample, can interact with a peroxidatively active substance in the test sample and undergo a detectable or measurable color transition to establish the presence or concentration of the peroxidatively active substance in the test sample.

Another object of the present invention is to provide a new and improved test device for interaction with a peroxidatively active substance in a test sample to produce a visible change, such as a change in color, of the test device, indicative of the concentration of the peroxidatively active substance in the test sample.

Another object of the present invention is to provide a composition and test device that are sensitive to low concentrations of a peroxidatively active substance, maintain an essentially constant pH during storage, and are sufficiently stable to essentially eliminate false positive assay results for a peroxidatively active substance resulting from a premature interaction between the indicator dye and the hydroperoxide.

Still another object of the present invention is to provide a stable indicator reagent composition capable of undergoing a detectable or measurable color transition upon contact with a peroxidatively active substance, wherein the indicator reagent composition comprises an indicator dye; a hydroperoxide; a buffer; and a bicyclic amine borate compound having the general structural formula:

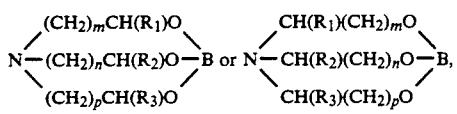

wherein $R_1$, $R_2$ and $R_3$ are, independently, methyl groups or ethyl groups, and m, n and p are numerals ranging from one to about three.

The above and other objects and advantages and novel feature of the present invention will become apparent from the following detailed description of the preferred embodiments of the present invention illustrating the indicator reagent composition, the test device, and the assay of liquid test samples for a peroxidatively active substance.

DETAILED DESCRIPTION OF THE INVENTION

In accordance with the method of the present invention, the qualitative or quantitative assay for a peroxidatively active substance, such as hemoglobin, a hemoglobin derivative, an erythrocyte, myoglobin, and combinations thereof, in urine and other test samples is accomplished by utilizing a stable indicator reagent composition comprising an indicator dye; a hydroperoxide; a bicyclic amine borate compound including pendant methyl group or ethyl groups; and a buffer. The indicator reagent composition of the present invention sufficiently stabilizes the indicator dye to essentially eliminate premature oxidation of the indicator dye by the hydroperoxide prior to contact between the indictor reagent composition and the test sample. However, the indicator dye, after contacting a test sample including a peroxidatively active substance, readily undergoes a detectable or measurable color transition in response to an interaction with the hydroperoxide that is mediated by the peroxidatively active substance in the test sample.

In addition, the amine borate compound included in the indicator reagent composition of the present invention is sufficiently resistant to hydrolysis such that the pH of the indicator reagent composition, and the pH of the test pad incorporating the indicator reagent composition, remains essentially constant during extended exposure to high humidity conditions. Therefore, the color transition resulting from the peroxidatively active substance-mediated interaction between the indictor dye and the hydroperoxide is more spectacular. Accordingly, the accuracy and the sensitivity of the assay to a low concentration of a peroxidatively active substance are increased.

The improved accuracy and increased sensitivity to low levels of a peroxidatively active substance afforded by the method of the present invention are especially useful in urine assays for occult blood. A commercially-useful urine assay for occult blood must include a stable indicator reagent composition, must be sensitive and preferably is resistant to ascorbic acid interferences. The stability and sensitivity requirements for a useful occult blood assay have been defined. For example, a sensitivity of a least 1 part occult blood per trillion parts of urine sample, or equivalently, for 0.015 mg (milligrams) hemoglobin per deciliter of urine or $2 \times 10^{-9}$ moles of hemoglobin per liter (L) of urine, is required.

In addition, as previously discussed, ascorbic acid and the ascorbate ion are common interferents with diagnostic tests based on redox indicator dyes. Ascorbic acid interference in the assay of urine for occult blood is well known in the art and preferably is eliminated. Ascorbic acid interferes with the oxidation of the indicator dye, and therefore ascorbic acid in a test sample produces an apparent negative result for a peroxidatively active substance. "Ascorbate resistance" therefore is defined as a negligible interference with the color transition of the indicator dye when a urine sample contains as much as approximately 50 mg (milligrams) ascorbic acid per deciliter (dL) of sample.

Present day commercial assays for a peroxidatively active substance, like occult blood, can detect hemoglobin concentrations in urine as low as about 0.015 mg/dL. The urine of a healthy individual is substantially free of hemoglobin. Therefore, detecting such a low concentration of hemoglobin in urine is clinically important because hemoglobin in the urine can signify a diseased or damaged condition that should be investigated further. Accordingly, and as will be discussed more fully hereinafter, the method and device of the present invention accurately assay for a low concentration of a peroxidatively active substance in urine. The composition used in the method and device of the present invention utilize a stable indicator reagent composition that undergoes a color transition only in response to the concentration of the peroxidatively active substance in the test sample, thereby providing sensitive and reliable assay for a peroxidatively active substance.

Furthermore, it will become apparent that in addition to assaying urine, the method and device of the present invention also can be used to determine the presence or quantitative concentration of a peroxidatively active substance in blood plasma or serum, feces, and gastrointestinal contents, e.g.; vomit and more generally, the peroxidatively active substance concentration of many other biological fluids and semisolids as well. In general, any aqueous test sample, or test sample that is soluble in an aqueous solvent, can be assayed. To achieve the full advantage of the present invention, the composition of the present invention is employed in dry phase test strip to determine the presence or concentration of a peroxidatively active substance in urine or other test samples.

Surprisingly and unexpectedly, it has been found that including a bicyclic amine borate compound having pendant methyl groups or ethyl groups in an indicator reagent composition further comprising an indicator dye, a hydroperoxide and a buffer substantially increases the stability of the indicator reagent composition by stabilizing the indicator dye. The indicator reagent composition of the present invention essentially eliminates the present day problems of false positive assays for a peroxidatively active substance and of decreased assay sensitivity due to an increased pH of the indicator reagent composition and test pad resulting from hydrolysis of the particular bicyclic amine borate used in the prior art. As will be discussed more fully hereinafter, the amine borate compounds found to stabilize the indicator dye and to effectively resist hydrolysis, and therefore to increase the stability of the composition and the accuracy, sensitivity and reliability of an assay for a peroxidatively active substance, are depicted by general structural formulas (I) and (II):

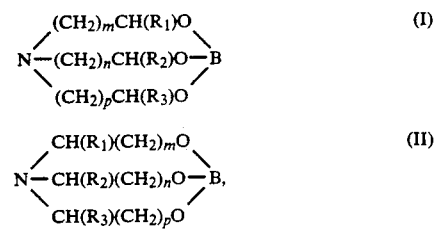

wherein $R_1$, $R_2$ and $R_3$ are, independently, methyl groups or ethyl groups, and m, n and p are numerals ranging from one to about three.

The method and test device utilizing the composition of the present invention provide a more accurate, trustworthy and clinically significant assay for a peroxidatively active substance because the indicator dye undergoes a color transition only in response to the amount of the peroxidatively active substance present in the test sample, and not to a premature interaction between the hydroperoxide and the indicator dye. Furthermore, the hydrolysis resistant amine borate included in the indicator reagent composition does not yield alkaline hydrolysis products that increase the pH of the indicator reagent composition, and consequently reduce the sensitivity of the assay. Accordingly, a fast, accurate, reproducible and trustworthy method of assaying for a peroxidatively active substance, performable at home or in the laboratory to yield essentially immediate assay results, is achieved.

The method of the present invention utilizes the ability of a peroxidatively active substance to catalyze, or otherwise participate in, a reaction wherein a hydroperoxide releases oxygen, and then to transfer the oxygen to oxidize an indicator dye. The oxidation of the indicator dye results in a color transition of the indicator reagent composition, with the degree and intensity of the color transition being directly proportional to the concentration of the peroxidatively active substance in the test sample. Accordingly, the indicator reagent composition of the present invention includes a hydroperoxide and an indicator dye, wherein the indicator dye undergoes a color transition upon conversion to its oxidized form by the mediation of the hydroperoxide and a peroxidatively active substance present in the test sample.

In accordance with an important feature of the present invention, the indicator dye is stabilized by a hydrolysis-resistant amine borate. In the prior art, Lam theorized that the hydroperoxide and the amine borate formed a complex that is sufficiently stable to preclude an interaction between the hydroperoxide and the indicator dye prior contact with a test sample including a peroxidatively active substance. However, it has been found that the amine borate stabilizes the indicator dye and precludes a premature interaction between the indicator dye and the hydroperoxide. Surprisingly and unexpectedly however, the reactivity of the stabilized indicator dye with the hydroperoxide in the presence of a peroxidatively active substance is not decreased.

The indicator reagent composition also can optionally include an ingredient to eliminate ascorbate interference with the assay for the peroxidatively active substance. Ascorbate resistance is imparted to a test device by the addition of a metal ion complex to the indicator reagent composition. However, metal ion complexes, like a ferric complex or a cobalt (III) complex, possess inherent peroxidative activity. Therefore the metal ion complex can behave in a similar manner to a peroxidatively active substance, like hemoglobin, and catalyze, or otherwise participate in, the color-forming hydroperoxide oxidation of the indicator dye. Accordingly, the indicator dye can be oxidized prematurely to give a false positive assay result. U.S. Pat. No. 4,587,220 to Mayambala-Mwanika et al discloses the use of particular ferric ion complexes to substantially alleviate the problems of reduced indicator reagent composition stability and of false positive assay results. As will be discussed more fully hereinafter, the indicator reagent composition of the present invention also can include a particular buffer compound that effectively counteracts the peroxidative activity of the metal ion complex in order to provide a more stable indicator reagent composition that yields an accurate and reliable assay for a peroxidatively active substance.

The indicator dye included in the indicator reagent composition is limited only in that the indicator dye is capable of undergoing a detectable response, and preferably a chromogenic response, in the presence of a hydroperoxide and a peroxidatively active substance. Accordingly, the indicator dye preferably is a redox indicator that undergoes a color transition upon conversion from its reduced state to its oxidized state by oxygen liberated from the hydroperoxide by the peroxidatively active substance. The indicator dye should be sufficiently stable, or stabilized, such that both a hydroperoxide and a peroxidatively active substance are present before a color transition occurs. To achieve the full advantage of the present invention, the indicator dye undergoes a color transition through various detectable and measurable degrees and intensities of color such that the degree or intensity of the color transition can be correlated to the concentration of a peroxidatively active substance in a test sample.

Several indicator dyes are suitable for use in the composition of the present invention, and generally include compounds that are oxidized relatively easily to yield deeply-colored oxidation products. Suitable classes of indicator dyes include, but are not limited to, the benzidine-type indicator compounds and the heterocyclic azine indicator compounds. Examples of the heterocyclic azine indicator compounds include, but are not limited to, bis-(N-ethylquinol-2-one)-azine and (N-methylbenzthiazol-2-one)-(1-ethyl-3-phenyl-5-methyl-triazol-2-one)-azine. The benzidine-type indicator compounds include, but are not limited to, for example, benzidine; o-tolidine; 3,3',5,5=-tetra(lower alkyl)benzidine; o-dianisidine; 2,7-diaminofluorene; and mixtures of these and other suitable indicator dyes. The term "lower alkyl", as used above, is defined as an alkyl moiety having from one to about six carbon atoms, including methyl, ethyl, n-propyl, isopropyl and the various butyl, pentyl and hexyl isomers. To achieve the full advantage of the present invention, the redox indictor, 3,3',5,5=-tetramethylbenzidine (TMB), is included in the indicator reagent composition.

The indicator dye usually is present in the indicator reagent composition in a concentration of from about 5 mM (millimolar, or millimoles of indicator dye per liter of indicator reagent composition) to about 60 mM, and preferably in a concentration of from about 20 mM to about 40 mM. It should be understood that the amount of indicator dye in the indicator reagent composition can be less than about 5 mNM, or greater than about 60 mM, depending upon the intensity of the color transition that a particular indicator dye undergoes upon oxidation. In general, the amount of indicator dye included in the indicator reagent composition is limited only in that the indicator dye must undergo a detectable color transition for a qualitative assay or, for a quantitative assay, must undergo a measurable color transition in proportion to the amount of peroxidatively active substance in the test sample.

In accordance with another important feature of the present invention, the indicator reagent composition also includes a hydroperoxide. The hydroperoxide is a compound capable of liberating free oxygen. The free oxygen in turn oxidizes the indicator dye to cause a color transition of the indicator reagent composition. The peroxidatively active substance present in the test sample catalyzes the liberation of free oxygen from the hydroperoxide and transfers the oxidative equivalent to the indicator dye, therefore initiating the color transition of the indicator dye.

Accordingly, a hydroperoxide included in the indicator reagent composition of the present invention should be sufficiently stable such that free oxygen is not liberated in the absence of a peroxidatively active substance. In addition, the hydroperoxide should possess a sufficiently low vapor pressure such that the hydroperoxide does not evaporate, or sublime, from the indicator reagent composition during storage, or after the indicator reagent composition is incorporated into a carrier matrix of a test pad of a dry phase test strip. Furthermore, the hydroperoxide should demonstrate a sufficient sensitivity to detect 1 part of hemoglobin in one trillion parts of test sample in the assay of urine for occult blood.

Therefore, a hydroperoxide useful in the indicator reagent composition of the present invention is selected from among the many well known hydroperoxides. However, the hydroperoxide must be capable of interacting with a peroxidatively active substance in the presence of a suitable indicator dye to produce a detectable response, such as a color transmission or a change in the amount of light absorbed or reflected by the test sample. Organic hydroperoxides are preferred. Specific examples of suitable hydroperoxides include, but are not limited to, cumene hydroperoxide; t-butyl hydroperoxide; diisopropylbenzene hydroperoxide; 1-hydroxycyclohexane-1-hydroperoxide; 2,5-dimethyl-hexane-2,5-dihydroperoxide; paramenthane hydroperoxide; 1,4-diisopropylbenzene monohydroperoxide; p-t-butylisopropylbenzene hydroperoxide; 2-(α-hydroperoxyisopropyl)-6-isopropylnaphthalene; tetralin hydroperoxide and combinations thereof. In the assay of urine for occult blood, 1,4-diisopropylbenzene dihydroperoxide (DBDH) is the preferred hydroperoxide because of the stability, sensitivity, and nonvolatility of DBDH.

The concentration of a hydroperoxide included in the indicator reagent composition ranges from about 5 mM to about 100 mM, and preferably from about 25 mM to about 75 mM. The specific amount of a particular hydroperoxide included in the indicator reagent composition is dependent upon the physical and chemical properties of the particular hydroperoxide, such as volatility, stability and sensitivity towards a peroxidatively active substance.

When a composition including only a hydroperoxide and an indicator dye is used in a method to assay a test sample for a peroxidatively active substance definite disadvantages become apparent. As previously stated, the hydroperoxide is included in the composition as an oxygen source for the oxidation of the indicator dye through a combined action of the peroxidatively active substance and the hydroperoxide. However, the combination of an indicator dye and a hydroperoxide also can result in a false positive assay for a peroxidatively active compound due to premature oxidation of redox indicator dye by the hydroperoxide. For example, a chloroform solution including a hydroperoxide and o-tolidine dye produced a black color in about two hours due to oxidation of the o-tolidine dye.

Accordingly, premature indicator dye oxidation by the hydroperoxide can introduce severe limitations on the stability of a dry phase test strip and on the process used to manufacture a dry phase test strip. For example, composition ingredients had to be incorporated into the carrier matrix in two steps, wherein the first step includes incorporating the hydroperoxide and the second step includes incorporating the indicator dye. Consequently, wet phase assays for a peroxidatively active substance employing a redox indicator dye, a hydroperoxide and a metal ion complex are unavailable because of a large background oxidation of the indicator dye. Likewise, dry phase test strips incorporating a redox indicator, a hydroperoxide and metal ion complex provided false positive assay results.

Surprisingly and unexpectedly, it has been found that including a bicyclic amine borate compound having pendant methyl groups or ethyl groups in an indicator reagent composition that further includes an indicator dye, a hydroperoxide and a buffer sufficiently stabilizes the indicator dye such that the indicator reagent composition can be used in a dry phase test strip to accurately assay a test sample for a peroxidatively active substance. In general, an amine borate compound useful in the composition of the present invention is depicted by general structural formula (I) and (II):

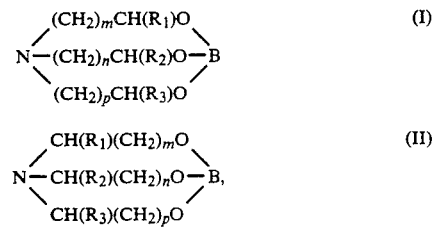

wherein $R_1$, $R_2$ and $R_3$ are, independently, methyl groups or ethyl groups, and m, n are numerals ranging from one to about three. To achieve the full advantage of the present invention, triisopropanolamine borate is included in the indicator reagent composition to further stabilize the indicator dye. Triisopropanolamine is an amine borate of general structural formula (I) wherein $R_1$, $R_2$ and $R_3$ each are methyl groups and the m, n and p each are one.

A bicyclic amine borate of general structural formula (I) or (II) is included in the indicator reagent composition in a concentration ranging from about 25 mM to about 400 mM, and preferably in a concentration ranging from about 50 mM to about 300 mM. To achieve the full advantage of the present invention, the bicyclic amine borate is included in the indicator reagent composition in a concentration ranging from about 75 mM to about 150 mM.

As previously discussed, Lam disclosed in U.S. Pat. No. 4,071,318 that an amine borate compound having the general structural formula (III):

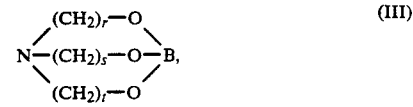

wherein r, s and t are integers ranging from 1 to 4, was included in an indicator reagent composition to increase the stability of a hydroperoxide, and to reduce premature oxidation of the indicator dye. Lam theorized that these amine borate compounds possess a unique geometry and electronic configuration, such that the electron-rich nitrogen atom of the amine borate couples with the proton of the hydroperoxide, and the electron-deficient boron atom couples with the residue of the hydroperoxide. Consequently, an amine borate of general structural formula (III) can complex with a hydroperoxide to prevent the hydroperoxide from interacting with the indicator dye prior to contact with the test sample.

However, it has been discovered that the amine borates do not complex with and stabilize the hydroperoxide, but rather stabilize the indicator dye, possibly by complexing with the indicator dye. Furthermore, the amine borates disclosed by Lam hydrolyze upon exposure to environmental humidity. Accordingly, hydrolysis destroys the prior art bicyclic amine borate, and the indicator dye is available to interact with the hydroperoxide and produce a premature background color. In addition, the products of the amine borate hydrolysis are alkaline. The alkaline hydrolysis products then increase the pH of the indicator reagent composition incorporated into the test strip. This pH increase results in a less spectacular, and a less differentiable, color transition in the test pad because the degree and intensity of the color transition is pH dependent. Consequently, assay sensitivity is decreased because differentation and resolution of the color transition is less dramatic.

Therefore, and in accordance with an important feature of the present invention, an amine borate of general structural formula (I) or (II) is included in the indicator reagent composition of the present invention. The amine borates of general structural formula (I) and (II), having pendant methyl groups or ethyl groups, stabilize the indicator dye and are resistant to hydrolysis. Accordingly, an amine borate of general structural formula (I) or (II) increases the stability of the indicator reagent composition. In addition, therefore, the sensitivity of the assay is increased because the amine borate resists hydrolysis and alkaline hydrolysis products are not generated.

An amine borate compound of general structural formula (I), such as triisopropanolamine borate, is especially preferred because the pendant methyl groups or ethyl groups are positioned on carbon atoms adjacent to the oxygen atoms. Therefore, the pendant methyl or ethyl groups more effectively hinder, sterically, the hydrolysis of the boron-oxygen bond of the amine borate. As will be demonstrated more fully hereinafter, the degree of stability imparted to the indicator reagent composition by including a hydrolysis-resistant amine borate of general structural formula (I) or (II) in the indicator reagent composition is both surprising and unexpected.

Furthermore, in addition to the indicator dye, the hydroperoxide and the hydrolysis-resistant amine borate, the indicator reagent composition also includes a suitable buffer. Test samples often have a pH outside the desired pH range for the assay of interest and therefore a buffer is added to the test composition. Accordingly, it has been demonstrated that any of various known types of buffers can be included in the indicator reagent composition of the present invention. The buffer is especially important in a commercially-acceptable dry phase test strip that resists the effects of urine pH and urine specific gravity. The function of the buffer is to maintain the indicator reagent composition at a proper pH to stabilize the indicator reagent composition and to produce the desired color transition in the indicator dye during the assay.

A buffer is included in the indicator reagent composition of the present invention usually in a concentration of between about 50 mM and about 600 mM, although in particular situations the concentration of the buffer can be above or below this range. It has been found that for optimum assay results, the pH of the indicator reagent composition generally should be maintained at a slightly acidic to a neutral pH value. Therefore, a pH of from about 5 to about 7, and preferably of from about 6 to about 7, provides a more spectacular and a more easily differentiable color transition in the assay for a peroxidatively active substance.

In contrast, present day assay methods for a peroxidatively active substance often are performed at a slightly alkaline pH because the hydrolysis of a prior art amine borate included in the indicator reagent composition yields alkaline hydrolysis products that increase the pH of the surface of the test pad. Surprisingly and unexpectedly, utilizing an indicator reagent composition of the present invention, including a hydrolysis-resistant amine borate compound of general structural formula (I) or (II), demonstrates sufficient stability such that the indicator reagent composition can be buffered to maintain an acidic to a neutral pH and to achieve a more spectacular color transition.

For example, the prior art teaches that when a ferric ion complex, like the ferric ion complex of N-(2-hydroxyethyl)ethylenediaminetriacetic acid (Fe—HEDTA), is included in the indicator reagent composition to provide the desired ascorbate resistance, the indicator reagent composition is buffered above a pH of 6.5, such as at a pH range of 6.7 from 7.1. Most preferably, the pH is buffered at 6.80 to 6.82. This pH range provides the best balance of sensitivity, stability and ascorbate resistance when assaying urine samples exhibiting highly variable pH values and specific gravity. If the pH of the indicator reagent composition is increased due to alkaline hydrolysis products of the amine borate, the sensitivity of the assay is reduced.

In accordance with an important feature of the present invention, it has been found that a phosphorus compound of general structural formula (IV) or (V):

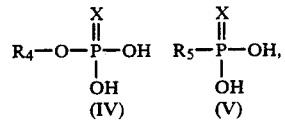

wherein $R_4$ and $R_5$ is selected from the group consisting of hydrogen, an unsubstituted or a substituted alkyl moiety including from one to about twelve carbon atoms, an unsubstituted or a substituted aromatic moiety and a residue of an aliphatic or an aromatic polyhydric compound; and wherein X is O, S or NH, can be used as the buffer in the indicator reagent composition of the present invention.

A phosphorus compound of general structure (IV) or (V) is included in the indicator reagent composition of the present invention as a buffer in a concentration ranging from 50 mM to about 600 mM, and preferably from about 100 mM to about 400 mM. To achieve the full advantage of the present invention, the phosphorus compound is present in a concentration ranging from about 150 mM to about 300 mM. As will be discussed more fully hereinafter, when present in a concentration of at least 50 mM, a phosphorus compound of general structural formula (IV) or (V), in addition to serving as a buffer, also provides improved stability to an indicator reagent composition that includes a compound to impart ascorbate resistance. In addition, a phosphorus compound of general structural formula (IV) or (V) can be included in the indicator reagent composition in a concentration greater than about 600 mM without adversely affecting either the indicator reagent composition or the method of the present invention. However, further buffering properties and further improvements in the stability of the indicator reagent composition are not demonstrated, and, therefore, the increased concentration of the phosphorus compound is wasted.

It is envisioned that the oxo (X=O), the thio (X=S) and the imino (X=NH) derivatives of the phosphorus compounds of general structural formulas (IV) and (V) are useful as buffers and to further improve the stability in the indicator reagent composition of the present invention. A preferred buffer that provides a more stable indicator reagent composition is a phosphorus compound of general structural formula (IV) or (V) having at least two free acid functionalities. Accordingly, the phosphorus compound of general structural formula (IV) wherein $R_4$ is hydrogen, i.e., phosphoric acid, and the phosphorus compound of general structural formula (V) wherein $R_5$ is hydrogen, i.e., phosphonic acid, are useful in the composition of the present invention.

It also has been found that the substituent $R_4$ on the phosphorus compound of general structural formula (IV) or the substituent $R_5$ on the phosphorus compound of general structural formula (V) can be an aliphatic moiety including from one to about twelve carbon atoms, such as ethyl dihydrogen phosphate. Furthermore, as the number of carbon atoms included in the aliphatic moiety increases, the more effectively a phosphorus compound of general structural formula (IV) or (V) buffers and stabilizes the indicator reagent composition of the present invention. Accordingly, a phosphorus compound of general structural formula (IV) or (V) wherein $R_4$ or $R_5$ is an aliphatic moiety including from about 5 to about 10 carbon atoms is preferred. A phosphorus compound of general structural formula (IV) or (V) wherein $R_4$ or $R_5$ is an aromatic moiety, like phenyl, also is useful as a buffer in the indicator reagent composition. The aromatic moiety can be a carbocyclic or a heterocyclic aromatic moiety, and includes aromatic moieties having fused rings. For example, the aromatic moiety can be derived from, but is not limited to derivation from, benzene, naphthalene, pyrrole, furan, pyrimidine, thiophene, pyridine, pyrazine, indole, quinoline, carbazole, purine, isoquinoline, isothiazole, isoxazole, and other similar carbocyclic and heterocyclic aromatic compounds. Specific examples include phenyl dihydrogen phosphate and phenyl phosphonic acid. More specifically, a phosphorus compound useful in the present invention is depicted by structural formulas (VI) and (VII), wherein Y is CH or N; and by structural formulas (VIII) and

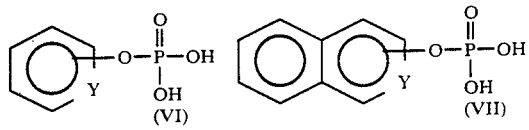

(IX), wherein Z is NH, O or S.

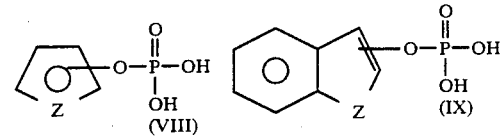

The aliphatic moiety or the aromatic moiety of the phosphorus compound of general structural formula (IV) or (V), $R_4$ or $R_5$ respectively, also can include a substituent group, or substituent groups, without adversely affecting the ability of the phosphorus compound to buffer and stabilize the indicator reagent composition of the present invention. The substituent group, or groups, can be positioned on any carbon of the aliphatic moiety, or at any position of the aromatic moiety, without adversely affecting the indicator reagent composition in an assay for a peroxidatively active substance. Substituent groups that can be included on the aliphatic moiety or on the aromatic moiety of the phosphorus compounds of general structural formulas (IV) and (V) include, but are not limited to, nitro (—$NO_2$), like in p-nitrophenyl dihydrogen phosphate; cyano (—CH); halo (—Cl,—Br); amino (—$NH_2$); substituted amino (—$NHR_6$, —$NR_7R_8$ wherein $R_6$, $R_7$ and $R_8$ are substituted or unsubstituted aromatic or alkyl moieties including from one to about ten carbon atoms); hydroxy (—OH); alkoxy (—$OR_9$ wherein $R_9$ is a substituted or an unsubstituted alkyl group including from one to about ten carbon atoms); aryloxy (—$OR_{10}$ wherein $R_{10}$ is a substituted or an unsubstituted carbocyclic or heterocyclic aromatic ring system); sulfonate (—$SO_3H$); carbonyl (—CO—$R_{11}$ wherein $R_{11}$ is hydrogen, hydroxyl, an alkyl group, an aryl group, an alkoxy group, an aryloxy group, or an amino group); or a combination thereof.

In accordance with an important feature of the present invention, the phosphorus compound of general structural formula (IV) or (V) including a substituent $R_4$ or $R_5$ that is a residue of an aliphatic or of an aromatic polyhydric compound is especially useful as a buffer. A polyhydric compound has at least two hydroxy functionalities and includes classes of compounds such as glycols, triols, polyls, saccharrides and hydroxyphenols. Examples of residues of polyhydroxy compounds that are useful as a substituent on a phosphorus compound of general structural formula (IV) or (V) include, but are not limited to, a residue of ethylene glycol, propylene glycol, butylene glycol, hexanediol, glycerol, neopentyl, glycol, diethylene glycol, dipropylene glycol, triethylene glycol, cyclopentanediol, cyclohexanediol, hydrobenzoin, fructose and sorbitol. Specific examples of phosphorus compounds of general structural formula (IV) or (V) that include a residue of a polyhydric compound include the compounds illustrated in structural formulas (X) thorough (XIII).

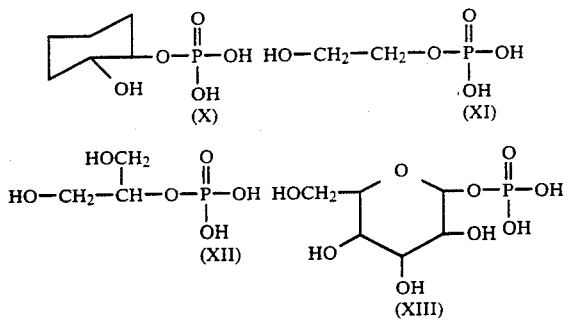

In particular, the compound of structural formula (X) includes the residue of cyclohexanediol, whereas the compound of structural formula (XI) includes the residue of ethylene glycol and the compound of structural formula (XIII) includes the residue of a monosaccharide, like glucose. The phosphorus compound illustrated as structural formula (XII), including a residue of glycerol, and termed glyceryl-2-phosphate, is the preferred phosphorus compound used as a buffer in the indicator reagent composition of the present invention.

Glyceryl-2-phosphate (XII) is a known buffer. However, as will be discussed more fully hereinafter, glyceryl-2-phosphate, in addition to acting as a buffer, also imparts improved stability to a composition of the present invention when a metal ion complex is included in the composition to provide ascorbate resistance. Other buffer agents known to those skilled in the art can be included in the indicator reagent composition for their buffering capabilities, but these buffers do not further stabilize an indicator reagent composition including a metal ion complex. For example, glyceryl-2-phosphate acts as a buffer and stabilizes the indicator reagent composition against the inherent peroxidative activity of a metal ion complex included for ascorbate resistance. Other known buffers do not stabilize the indicator reagent composition against the inherent peroxidative activity of metal ion complexes added for ascorbate resistance.

Accordingly, the phosphorus compound of general structural formulas (IV) or (V) can be used as the buffer. In addition, other well-known buffers such as acetate; phthalate; borate; trichloroacetate; sulfosalicylate; phosphate; tartarate; citrate; succinate; maleic acid; 2,2-bis(hydroxymethyl)-2,2′,2″-nitrilotriethanol; 1,4-piperazinebis(ethanesulfonic acid); 3,3-dimethylglutaric acid; 3-N-morpholinopropanesulfonic acid (MOPS); malonic acid; 1,3-bis[tris(hydroxymethyl)methylamino]propane (Bistris); tris(hydroxymethyl)aminomethane (Tris); tris(hydroxymethyl)aminomethane-maleic acid (Trismaleate); tris(hydroxymethyl)aminomethane-malonic acid (Tris-malonate); 3-[N-tris(hydroxymethyl)methylamino]-2-hydroxypropanesulfonic acid (TAPSO); 2-[tris(hydroxymethyl)methylamino]ethanesulfonic acid (TES); 1,4-piperazinebis(ethanesulfonic acid) (PIPES); 4-morpholinoethanesulfonic acid) (MES); N-2-hydroxyethylpiperazine-N′-2-ethanesulfonic acid (HEPES); and other suitable buffers as are well known in the art, or combinations thereof, can be used as the buffer in the indicator reagent composition of the present invention.

Therefore, the indicator reagent composition of the present invention, including an indicator dye, a hydroperoxide, an amine borate compound of general structural formula (I) or (II) and a buffer is utilized in an improved method to determine the presence or the concentration of a peroxidatively active substance in liquid test samples. It has been demonstrated that the indicator reagent composition is stable previous to contact with a liquid test sample, and then interacts with a peroxidatively active substance in the test sample to produce a differentiable and measurable color transition, either visually or by instrument. Furthermore, in addition to the essential ingredients described above, the indicator reagent composition of the present invention can include a sufficient amount of optional ingredients, like a metal ion complex to impart ascorbate resistance, such that the indicator dye changes color upon contact and interaction with the oxygen that is catalytically released from the hydroperoxide by the peroxidatively active substance. Accordingly, the color change accurately establishes the presence or concentration of a peroxidatively active substance in the test sample.

Therefore, in addition to the essential ingredients, the indicator reagent composition also can include, optionally, a metal ion complex to impart ascorbate resistance to the assay. In general, the metal ion complex facilitates oxidation of the ascorbate ion present in the test sample and thereby eliminates the ascorbate interference. Metal ions have inherent peroxidative activity, and, unless complexed, will interact with the hydroperoxide present in the indicator dye to change color. In addition, the prior art teaches that complexed metal ions, other than a complexed ferric ion, interact with a hydroperoxide and an indicator dye to cause color change.

Therefore, a metal ion that can eliminate ascorbate interference, when complexed, optionally can be included in the indicator reagent composition of the present invention. Accordingly, a suitable metal ion useful in the metal ion complex is selected from the group consisting of ferric ion, cobalt (III) ion, cupric ion, mercuric ion, stannic iron, nickel (II) ion, lead (II) ion, manganese (III) ion, cadmium (II) ion, zinc (II) ion, molybdenum (V) ion, chromium (IV) ion, vanadium (III) ion and combinations thereof. In addition, metal ions having a valence state greater than (III) also can be used as the metal ion, as long as the metal ion can be complexed sufficiently to prevent premature oxidation of the indicator dye. To achieve the full advantage of the present invention, the metal ion present in the metal ion complex is the ferric ion.

As previously stated, the metal ion must be complexed to preclude premature oxidation of the indicator dye. However, the identity of the complexing agent is not particularly limited and, for example, can include a polycarboxyalkylamine, like ethylenediaminetetraacetic acid or nitrilotriacetic acid; a polycarboxylic acid or salt, like citric acid, tartaric acid or gluconic acid; histidine; a polyhydroxy compound, like sorbitol; a lignosulfonate; a glucoheptonate; bis(dimethylglyoximato); salicylate complexes, like bissalicylaldehydeethylenediiminato; dithioate derivatives; polyethyleneamines, like triethyleneamine; (2-dimethylaminoethyl)aminecobalt (II); 2,4-pentanedione; a phenanthroline derivative; a dipyridine derivative, like triethylenepyridine amine; a polypeptide containing cysteine, glycine or histidine; proline or a proline derivative; a thiocrown ether, like 1,4,8,11,22,25-octathiacyclooctasane; a triphenylphosphine; or combinations thereof.

In particular, ferric ion complexes useful in the indicator reagent composition include, but are not limited to, the ferric ion polycarboxyalkylamine complexes, such as the ferric ion complexes of N-(2-hydroxyethyl)ethylenediaminetriacetic acid (Fe-HEDTA), ethylenediaminetetraacetic acid (Fe-EDTA), cyclohexylenediaminetetraacetic acid (Fe-CDTA), nitrilotriacetic acid (Fe-NTA), iminodiacetic acid (Fe-IMDA), ethylenediaminediacetic dipropionic acid (Fe-EDDP), hydroxyethyliminodiacetic acid (Fe-HIMDA), diethylenetriaminepentaacetic acid (Fe-DTPA), ethylenebis(oxyethylenenitrilo)tetraacetic acid (Fe-EGTA); N-(2-acetamido)iminodiacetic acid (Fe-ADA), or combinations thereof. The ferric ion polycarboxyalkylamine complexes are described more fully in U.S. Pat. No. 4,587,220, hereby incorporated by reference. Other suitable ferric ion complexes include ferric citrate, ferric gluconate, ferric glucoheptonate, ferric bissalicylaldehydeethylenediimminato, and ferric triethylenepyridine amine. Especially useful ferric ion complexes are Fe-HEDTA and Fe-EDTA. It also has been found that, if a metal ion complex other than a ferric ion complex is included in the indicator reagent composition, a phosphorus compound of general structural formula (IV) or (V) should be used as the buffer in the indicator reagent composition to reduce the inherent peroxidative activity of the metal ion complex.

The metal ion complex is included in the indicator reagent composition in an amount ranging from about 0 mM to about 50 mM, and preferably in the range of from about 1 mM to about 25 mM. When present in this amount, the metal ion complex essentially eliminates ascorbate interference in the assay of test samples including up to about 50 mg/dL (milligram per deciliter) ascorbate. In addition, it should be understood that a suitable metal ion complex, like Fe-HEDTA, can be commercially available, and therefore incorporated directly into the indicator reagent composition. Alternatively, the metal ion complex can be produced in situ during manufacture of the indicator reagent composition, such as by independently incorporating a metal ion salt, like ferric chloride hexahydrate (FeCl$_3$ 6H$_2$O), and an approximately equimolar amount of a complexing agent, like N-(2-hydroxyethyl)ethylenediaminetriacetic acid (HEDTA), into the indicator reagent composition to form the Fe-HEDTA ferric ion complex. When forming the metal ion complex in situ, the metal ion complex is formed before the uncomplexed metal ion can contact and interact with the hydroperoxide and the indicator dye.

In addition to the indicator dye, the hydroperoxide, the buffer and the amine borate compound of general structural formula (I) or (II), other optional ingredients, in addition to the metal ion complex, that do not materially alter the nature and the function of the four essential ingredients, and that do not interfere with the assay for a peroxidatively active substance, also can be included in the indicator reagent composition. For example, the indicator reagent composition optionally can include a compound to improve the wetting of the test pad of the test device by the test sample and to stabilize the oxidized indicator dye. This compound usually is an anionic surfactant or a nonionic surfactant. An anionic surfactant, such as a long carbon chain sulfate or sulfonate, like sodium dodecyl sulfate, dioctyl sodium sulfosuccinate and sodium dodecylbenzene sulphonate, is the preferred surfactant. Nonionic surfactants, such as an octoxynol, a nonoxynol or an ethoxylated fatty alcohol, also can be included in the indicator reagent composition of the present invention. The surfactant is included in the indicator reagent composition in a concentration of from 0 mM to about 200 mM, and preferably in a concentration of from about 50 mM to about 150 mM.

The indicator reagent composition also can include a polymeric material that improves the stability and uniformity of the color transition of the test device. Furthermore, when the ingredients of the indicator reagent composition are incorporated into the test pad from two separate solutions, the polymeric material helps separate the ingredients present in the first impregnation solution from interacting with the ingredients present in the second impregnation solution. Accordingly, the test strip demonstrates increased stability. Suitable polymeric materials include, but are not limited to, polyvinyl pyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone, such as PVP K-30, a polyvinylpyrrolidone of molecular weight 40,000 and available commercially from GAF Corp., New York, N.Y. The polymeric material generally is included in the indicator reagent composition in amounts ranging from 0% to about 5%, and preferably from about 1% to about 4%, by total weight of the indicator reagent composition.

In addition, to improve the color resolution and differentiation of the color transition in a chromogenic assay for a peroxidatively active substance, inert background dyes can be included in the indicator reagent composition. Suitable background dyes include, but are not limited to, ethyl orange (4-(4-diethylaminophenylazo)benzenesulfonic acid); Orange G (4-[2-hydroxy-(7,9 sodium disulfonate)-1-naphthylazo]benzene); disperse orange 11,13, or 25; calcomine orange; methyl orange; and orange (II) (4-(2-hydroxy-1-naphthylazo)benzenesulfonic acid); or combinations thereof. A background dye is included in the indicator reagent composition of the present invention in a concentration ranging from 0 mM to about 2 mM, and preferably ranging from about 0.1 mM to about 1.2 mM.

The indicator reagent composition also can include a promoter to achieve a more sensitive assay for a peroxidatively active substance in a test sample. Promoters are known in the art of assaying for a peroxidatively active substance and include quinolines and isoquinolines, and their derivatives. U.S. Pat. No. 3,975,161 disclosed a test strip comprising a bibulous carrier impregnated with a composition containing an organic hydroperoxide, an acid buffer, a chromogen, a wetting agent, a solid film-forming natural or synthetic polymeric substance and an isoquinoline or an isoquinoline derivative accelerator. In addition, the acid salts or adducts of quinoline and quinoline derivatives also have been described in U.S. Pat. No. 3,986,833 as potentiating agents in reagent compositions for the detection of peroxidatively active substances. U.S. Pat. No. 3,853,472 fully describes the quinolines and isoquinolines that are useful as promoters, and is hereby incorporated by reference.

Accordingly, isoquinoline, 4-bromoisoquinoline, 4-methylquinoline, 6-methoxyquinoline, 3-aminoquinoline and 5,6-benzoquinoline are the preferred promoters. To achieve the full advantage of the present invention, 4-methylquinoline, available under the brand name LEPIDINE® from Aldrich Chemical Co., Milwaukee, Wis., or 6-methoxyquinoline is used as the reaction promoter. A promotor generally is included in the indicator reagent composition in a concentration ranging from 0 mM to about 150 mM, and preferably in a concentration ranging from about 25 mM to about 125 mM. It also should be understood that other optional ingredients, as are well known to those skilled in the art of diagnostic assays, also can be included in the indicator reagent composition.

The carrier vehicle for the ingredients included in the indicator reagent composition includes water. However, because of the limited water solubility of particular ingredients included in the indicator reagent composition, organic solvents such as methanol, ethanol, isopropyl alcohol, acetone, dimethylformamide, dimethylsulfoxide, acetonitrile, ethyl acetate and similar solvents can be included in the carrier vehicle. The selection of a suitable organic solvent or solvents, in addition to water, to include in the carrier vehicle of the indicator reagent composition is within the capability of those skilled in the art of designing diagnostic assays.

The amount of organic solvent present in the indicator reagent composition generally is in the range of from 0% to about 90%, and preferably from about 10% to about 70%, by weight of the carrier vehicle. A carrier solvent comprising water and an organic solvent, like ethanol or acetonitrile, is especially preferred because a carrier matrix impregnated with the indicator reagent composition can be dried within a few to several minutes.

As previously described, the indicator reagent composition undergoes a color transition upon contact with a test sample to demonstrate the presence of a peroxidatively active substance. Furthermore, the intensity and degree of the color transition are used to determine the quantitative concentration of a peroxidatively active substance in the test sample by comparing or correlating the color produced by the test sample to colors produced by solutions having a known concentration of the peroxidatively active substance. In accordance with an important feature of the present invention, it has been demonstrated that an indicator reagent composition of the present invention provides a sufficiently resolved and differentiated color transition such that the amount of a peroxidatively active substance in a test sample can be measured and accurately determined without the use of color-measuring instruments, such as spectrophotometers or colorimeters. However, if desired, such color-measuring instruments can be used to measure the difference in color degree and intensity between the test sample and a solution having a known concentration of a peroxidatively active substance.

Accordingly, an assay for a peroxidatively active substance that utilizes an indicator reagent composition of the present invention improves the accuracy and reliability of the assay and also increases physician confidence in the assay. Additionally, because of the number of urine assays for a peroxidatively active substance being performed at home by the untrained patient, as opposed to trained physicians or technicians in the laboratory, it is imperative to provide accurate and reliable quantitative assay methods for the peroxidatively active substance content in the urine.

To demonstrate the new and unexpected results achieved by the method of the present invention, an indicator reagent composition including an indicator dye, a hydroperoxide, an amine borate of general structural formula (I) or (II) and a buffer was used in a dry phase test strip assay for a peroxidatively active substance. The dry phase test strip assay utilizing the indicator reagent composition of the present invention is performed in accordance with methods well known in the art. In general, the assay for peroxidatively active substance is performed by contacting the urine or other test sample with an analyte detection device that includes the indicator reagent composition. The analyte detection device can be dipped into the test sample, or the test sample can be applied to the analyte detection device dropwise. The resulting change in color of the analyte detection device demonstrates the presence of a peroxidatively active substance; and, if so designed, the resulting color transition can be compared to a standardized color chart to provide a quantitative measurement of the concentration of a peroxidatively active substance in the urine or test sample.

Typically, the analyte detection device is a reagent impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or a nonbibulous carrier matrix incorporating the indicator reagent composition. In general, the carrier matrix is an absorbent material that allows the test sample to move, in response to capillary forces, through the carrier matrix to contact the indicator reagent composition and produce a detectable or measurable color transition.

The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and non-asorptive substances are not suitable for use as the carrier matrix of the present invention. The carrier matrix can be of different chemical compositions or a mixture of chemical composition. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bilbulous filter paper or nonbibulous polymeric films.

If the test strip is designed to assay for a peroxidatively active substance in a test sample, the carrier matrix can be any bibulous or nonbibulous material that allows permeation by the test sample to saturate the test pad of the test strip that is impregnated with the indicator reagent composition. To achieve the full advantage of the present invention, in the assay for a peroxidatively active substance in a test sample, the carrier matrix is a hydrophilic, bibulous matrix, including cellulosic materials, such as paper, and preferably filter paper. Filter paper possesses all of the qualities required of a bibulous matrix of the present invention, plus the advantages of abundant supply, favorable economics, and a variety of suitable grades. Filter paper has been found to be extremely satisfactory for use as a matrix material for suspending and positioning both the essential ingredients and any optional ingredients included in the indicator reagent composition.

To achieve the full advantage of the present invention, the indicator reagent composition is impregnated into a suitable carrier matrix and utilized in a dry phase test strip for the assay of a peroxidatively active substance in a test sample. The method of the present invention affords an economical, accurate and reliable assay for the presence or concentration of a peroxidatively active substance in a test sample that can be performed at home or in the laboratory. In addition, the method of the present invention allows detection, differentiation and measurement of a low concentration of a peroxidatively active substance in the test sample therefore making the assay more useful clinically.

In accordance with the method of the present invention, to perform a dry phase test strip assay for a peroxidatively active substance, an aqueous solution, including from about 50 mM to about 600 mM of a buffer, such as a phosphorus compound of general structural formula (IV) or (V); from 25 mM to about 400 mM of an amine borate of general structural formula (I) or (II); from 0 mM to about 50 mM of a metal ion complex; from 0 mM to about 200 mM of a surfactant; and any other desired optional ingredients or solvents, first is prepared. This aqueous solution then is adjusted to a pH of from about 6 to about 7 with a suitable organic or mineral acid, such as 1N hydrochloric acid. A bilbulous matrix, such as filter paper, then is saturated and impregnated with the aqueous solution by immersing or by spraying the aqueous solution onto sheets or precut strips of the filter paper.

Then, after removing the aqueous solvent by drying in an air oven at a temperature of from about 40° C. to about 100° C. for about 5 minutes, the filter paper is saturated and impregnated with an ethanolic solution including from about 5 mM to about 60 mM of an indicator dye; from about 5 mM to about 100 mM of a hydroperoxide; from 0% to about 5% of a polymeric material; from 0 mM to about 150 mM of a promoter; and any other desired optional ingredients or solvents, like background dyes, either by immersion or by spraying. After a second oven drying at about 40° C. to about 100° C. for approximately 5 minutes, the twice-impregnated filter paper is cut to an appropriate size, such as a pad having dimensions from about 0.25 cm by about 0.5 cm to about 0.5 cm by about 1.0 cm.

It should be understood that is is well within the experimental techniques of those skilled in the art of preparing test devices to determine the proper balance between size of reagent pad, the strength of reagent impregnating solutions, the amount of test sample, and the method of introducing the test sample to the test strip, such as by pipetting rather than dipping, in order to design a quantitative assay for a peroxidatively active substance utilizing the method and composition the present invention.

The dried, twice-impregnated filter paper then is secured to an opaque or transparent hydrophobic plastic handle with double-sided adhesive tape. The resulting test strip then is dipped into a fresh, uncentrifuged urine sample for a sufficient time to saturate the test pad with the sample. After waiting a predetermined time, such as from about 15 secs. to about 60 secs., the test strip is examined, either visually or by instrument, for a response. The color transition, if any, of the test pad reveals the presence or concentration of a peroxidatively active substance in the urine sample.

In many cases, simple visual observation of the test strip provides the desired information. If more accurate information is required, a color chart bearing color spots corresponding to various known concentrations of a peroxidatively active substance can be prepared for the particular indicator reagent composition used in the test strip. The resulting color of the test strip after contact with the urine sample then can be compared with the color spots on the chart to determine the concentration of a peroxidatively active substance in the test sample. If a still more accurate determination is required, a spectrophotometer or colorimeter can be used more precisely determine the degree of color transition. In addition, the dry phase test strip assay can be made quantitative by employing spectrophotometric or colorimetric techniques, as opposed to visual techniques, in order to reliably and more accurately measure the degree of color transition, and therefore more accurately measure the concentration of a peroxidatively active substance in the test sample, especially at lower concentrations, such as below 0.015 mg/dL.

In accordance with one embodiment of the present invention, the following dry phase test strips were prepared to perform a dry phase assay for a peroxidately active substance. A strip or a sheet of a carrier matrix, like filter paper, such as WHATMAN 3MM, available from Whatman Inc., Maidenhead, Kent U.K., first was immersed into an aqueous solution including:

| INDICATOR REAGENT COMPOSITION Formulation #1 First Immersion Solution | |
|---|---|
| Ingredient | Concentration |
| Buffer | 200 mM |
| Ferric chloride (Metal ion) | 5.1 mM |
| N-(2-hydroxyethyl)ethylene-diaminetetraacetic acid (Complexing agent for the metal ion) | 5.1 mM |
| Triisopropanolamine borate (Amine borate) | 250 mM |
| Sodium Dodecyl Sulfate (Surfactant) | 28 mM |
| Hydrochloric Acid (1N) | to adjust pH to 6.7 to 6.8. |

The buffer included in the first immersion solution of the indicator reagent composition of Formulation #1 was either malonic acid, with the pH adjusted to about 6.8, or glyceryl-2-phosphate, with the pH adjusted to about 6.7.

The once impregnated-filter paper matrix then was dried in an oven having a temperature ranging from about 45° C. to about 60° C. After drying, the once-impregnated filter paper then was immersed into an ethanolic solution including:

| Second Immersion Solution | |
| --- | --- |
| Ingredient | Concentration |
| Tetramethylbenzidine (TMB) (Indicator Dye) | 34.7 mM |
| Diisopropylbenzenedi-hydroperoxide (DBDH) (Hydroperoxide) | 65.0 mM |
| 4-Methylquinoline (Promoter) | 61.3 mM |
| Ethyl Orange (Inert Background Dye) | 0.69 mM |
| Orange G (Inert Background Dye) | 0.55 mM. |

The twice-impregnated filter paper matrix then was dried in an oven having a temperature ranging from about 40° C. to about 60° C.. The dried and twice-impregnated filter paper then was cut into a pad having dimensions of about 0.5 cm by about 0.5 cm to provide a test pad comprising a carrier matrix impregnated with an indicator reagent composition of the present invention.

In addition, it should be understood that the indicator reagent composition of the present invention demonstrates sufficient stability such that the carrier matrix can be impregnated by immersing the carrier matrix into an aqueous solution including all of the essential and optional ingredients of the indicator reagent composition. However, the two step method utilizing two immersions is preferred if a metal ion complex is included in the indicator reagent composition because contact between the indicator dye, the hydroperoxide and the metal ion complex is avoided, and therefore a premature interaction between these ingredients is precluded.

To demonstrate the new and unexpected results achieved by the method of the present invention, dry phase test strips incorporating an indicator reagent composition of the present invention (Formulation #1) were compared (a) to dry phase test strips incorporating an indicator reagent composition including a prior art amine borate and (b) to dry phase test strips incorporating an indicator reagent composition absent an amine borate in order to determine the relative stability of the test strips and to determine the change in pH of the test strips upon exposure to environmental humidity.

The individual dry phase test strips used in the comparative test were produced by a two immersion technique as described above. The test strips then were dipped into a standardized urine test sample including 0.045 mg/dL of hemoglobin. One minute after contacting the standardized urine sample, the reflectance of the test pad of the test strip was measured at 660 nm (nanometers) on an Advanced Research Rapid Scanner reflectance spectrometer, of the Diagnostics Division of Miles, Inc., Elkhart, Ind. The reflectance measurement represents the reactivity of a particular dry phase test strip to a urine sample including a standardized amount of a peroxidatively active substance. In general, the lower the reflectance measurement, or value, the greater the color development, and, therefore, the greater the concentration of a peroxidatively active compound in the test sample.

In addition, the stability of the individual dry phase test strips was demonstrated by comparing the reactivity of a dry phase test strip stored at 60° C. for two weeks to the reactivity of an identical dry phase test strip stored at −23° C. for two weeks. The test strips were dipped into a standardized urine sample containing 0.045 mg/dL of hemoglobin, then, one minute after dipping the test strip into the urine sample, the reflectance of the test strip was measured at 660 nm with an Advanced Research Rapid Scanner reflectance spectrometer. The change in percent reflectance between the stressed (i.e., stored at 60° C.) and unstressed (i.e., stored at −23° C.) test strips represents the stability of the test strip. The smaller the change in percent reflectance between the stressed test strip and the unstressed test strip after contacting the test sample, the greater the stability of the indicator reagent composition.

TABLE I summarizes the reactivity and stability data of stressed and unstressed dry phase test strips including an indicator reagent composition either absent an amine borate (EXS. 2 and 5), test strips including an amine borate of the prior art (triethanolamine borate, EX. 3), and test strips including an amine borate useful in the method and composition of the present invention (triisopropanolamie borate, Formulation #1, EXS. 1 and 4). In TABLE I, Example 1 shows the change in percent reflectance between a stressed and unstressed dry phase test strip that incorporates an indicator reagent composition of the present invention (Formulation #1) including triisopropanolamine borate as a stabilizer for the indicator dye and malonic acid as the buffer. The unstressed test strip exhibited a reflectance of 21.3% at 660 nm one minute after dipping the test strip into a standardized urine sample containing 0.045 mg/dL of hemoglobin. The stressed test strip demonstrated a reflectance of 35.6%. Accordingly, the difference in percent reflectance between the stressed and unstressed test strips was 14.3.

TABLE 1

STABILITY AND REACTIVITY OF DRY PHASE TEST STRIPS INCLUDING OR ABSENT AN AMINE BORATE

| EXAMPLE | BUFFER (pH) | AMINE BORATE INCLUDED IN INDICATOR REAGENT COMPOSITION | STABILITY DATA (CHANGE IN % REFLECTANCE AFTER 14 DAYS AT 60°) | CHANGE IN pH UPON EXPOSURE TO HUMIDITY |
| --- | --- | --- | --- | --- |
| 1 | Malonic Acid (6.8) | Triisopropanolamine Borate | 14.3 | 0.0 |
| 2 | Malonic Acid (6.8) | None | 30.1 | 0.0 |
| 3 | Malonic Acid (6.8) | Triethanolamine Borate (prior art) | 15.7 | 0.7 |
| 4 | Glyceryl-2-phosphate (6.7) | Triisopropanolamine Borate | 6.6 | 0.0 |

TABLE 1-continued
STABILITY AND REACTIVITY OF DRY PHASE TEST STRIPS
INCLUDING OR ABSENT AN AMINE BORATE

| EXAMPLE | BUFFER (pH) | AMINE BORATE INCLUDED IN INDICATOR REAGENT COMPOSITION | STABILITY DATA (CHANGE IN % REFLECTANCE AFTER 14 DAYS AT 60°) | CHANGE IN pH UPON EXPOSURE TO HUMIDITY |
|---|---|---|---|---|
| 5 | Glyceryl-2-phosphate (6.7) | None | 28.9 | 0.0 |

The change in percent reflectance in EX. 1 should be compared to the change in percent reflectance between the stressed and unstressed test strips in EX. 2. The indicator reagent composition incorporated into the test strips of EX. 2 was identical to the indicator reagent composition incorporated into the test strips of EX. 1, except that an amine borate was omitted from the composition. Consequently, the change in percent reflectance between the stressed and unstressed test strips increased to 30.1. Therefore, the test strips of EX. 2, absent an amine borate, are substantially less stable than the test strips of EX. 1, including a bicyclic amine borate having three pendant methyl groups. Likewise, the test strips used in EX. 3, incorporating an indicator reagent composition including a prior art amine borate, also are less stable than test strips incorporating an indicator reagent composition of the present invention as demonstrated by an increase in change of percent reflectance up to 15.7. Quantitatively, the composition of the present invention (EX. 1) is approximately 10% more stable than a prior art composition (EX. 3), and approximately 110% more stable than a composition absent an amine borate (EX. 2).

The test strips used in Examples 4 and 5 demonstrate an even greater stability resulting from an indicator regent composition of the present invention (Formulation #1) including glyceryl-2-phosphate as the buffer. Example 4 demonstrates that the change in percent reflectance between a stressed test strip and an unstressed test strip is only 6.6 percentage units when triisopropanolamine borate is included in the indicator reagent composition and glyceryl-2-phosphate is the buffer. Example 5 demonstrates an unacceptable 28.9 change in percent reflectance when an amine borate is omitted from the indicator reagent composition.

TABLE I also demonstrates that an amine borate useful in the present invention, i.e., triisopropanolamine borate, present in EX. 1 and EX. 4, maintains the test strip at a constant pH upon exposure of the test strips to approximately 55% relative humidity air at 74° F. for about 10 minutes. Example 3 shows that test strips including a prior art amine borate, i.e., triethanolamine borate, exhibited a pH change of 0.7 pH units after the exposure of the test strips to approximately 55% relative humidity air at 74° F. for about 10 minutes. The adverse effect of an increase in pH of the indicator reagent composition is shown in the reactivity of the test strips, wherein EX. 1 and EX. 4 gave more spectacular and differentiable color transitions at pH 6.8 and 6.7, respectively, than EX. 3 at pH 7.5, a pH value substantially removed from the optimum pH for the maximum color transition of the TMB indicator dye.

To further demonstrate that an indicator reagent composition of the present invention, including an amine borate compound of general structural formula (I) or (II) to stabilize the indicator dye, essentially eliminates the problem of a false positive assay, the indicator reagent composition of Formulation #2 was prepared. Then, test strips including the indicator reagent composition of Formulation #2 were manufactured. The tests strips were subjected to a stress test, then the amount of unreacted indicator dye remaining in the test strip was determined. The change in percent reflectance between a stressed test strip and an unstressed test strip was determined by using the test strips to assay a standardized urine sample.

| INDICATOR REAGENT COMPOSITION FORMULATION #2 (Preferred Embodiment) | |
|---|---|
| First Dip | |
| Glyceryl-2-phosphate (buffer) | 225 mM |
| 3-N-Morpholinopropanesulfonic acid (buffer) | 225 mM |
| Ferric chloride (metal ion) | 7.5 mM |
| N-(2-hydroxyethyl)ethylenediaminetriacetic acid (complexing agent for the metal ion) | 7.5 mM |
| Triisopropanolamine borate (amine borate) | 125 mM |
| Sodium Dodecyl Sulfate (SDS) (surfactant) | 100 mM |
| Second Dip | |
| Polyvinylpyrrolidone (polymeric material) | 2.5% by weight |
| 3,3'5,5'-Tetramethylbenzidine (TMB) (indicator dye) | 34.7 mM |
| 1,4-Diisopropylbenzene dihydroperoxide (DBDH) (hydroperoxide) | 65.0 mM |
| 4-Methylquinoline (LEPIDINE ®) (promoter) | 105 mM |
| 4-(4-Diethylaminophenylazo)-benzenesulfonic acid (Ethyl Orange) (inert background dye) | 0.69 mM |
| 4-(2-Hydroxy-(7,9-sodiumdisulfonate)-1-naphthylazo)-benzene (Orange G) (inert background dye) | 0.55 mM |
| Water and Ethanol (carrier vehicle) | q.s. |
| Adjust pH to 6.7 with 1 N HCl | |

The test results are summarized in TABLE II, wherein the preferred indicator reagent composition of the present invention (Formulation #2) was incorporated into the test strips used in Examples 12 and 13. In Examples 6 through 9, the buffer, morpholino-propanesulfonic acid (MOPS) was omitted from the indicator reagent composition, thereby leaving only glyceryl-2-phosphate (GPA) as the buffer. Furthermore, in Examples 6, 7, 10 and 11, the hydrolysis-resistant amine borate was omitted from the indicator reagent composition. Each test strip was dipped into a standardized urine test sample including 0.045 mg/dL of hemoglobin, then the reflectance was measured at 660 nm approximately one minute after contact between the test strip and the urine sample. The change in percent reflectance between the unstressed test strips and the stressed test strips is a measure of the stability of the indicator reagent composition, and consequently, a measure of the stability of the test strip. Identical test strips, both stressed and unstressed, were examined for the amount of unreacted TMB indicator dye remaining in the test pad by standard high pressure liquid chromatography (HPLC) techniques.

TIB amine borate, demonstrate a substantially increased stability compared to the test strips used in Examples 6 and 7, omitting a hydrolysis-resistant amine borate.

A similar comparison can be made between the test strips used in Examples 10 and 11, incorporating the indicator reagent composition absent the TIB amine borate, and between the test strips used in Examples 12 and 13, incorporating the indicator reagent composition of Formulation #2. The data demonstrate that even greater stability is imparted to the test strips by using

TABLE II

STABILITY OF TEST STRIPS

| EXAMPLE | BUFFER(S) | AMINE BORATE | STRESS CONDITIONS | CONCEN-TRATION TMB (ug/cm$^2$) | ACTUAL % REFLECTANCE | CHANGE IN % REFLECTANCE |
|---|---|---|---|---|---|---|
| 6 | GPA | None | 2 weeks at −23° C. | 201 | 23.07 | 28.86 |
| 7 | GPA | None | 2 weeks at 60° C. | 121 | 51.93 | |
| 8 | GPA | TIB | 2 weeks at −23° C. | 204 | 23.67 | 6.59 |
| 9 | GPA | TIB | 2 weeks at 60° C. | 172 | 30.26 | |
| 10 | GPA + MOPS | None | 2 weeks at −23° C. | 202 | 23.21 | 25.40 |
| 11 | GPA + MOPS | None | 2 weeks at 60° C. | 141 | 48.61 | |
| 12 | GPA + MOPS | TIB | 2 weeks at −23° C. | 201 | 22.61 | 4.30 |
| 13 | GPA + MOPS | TIB | 2 weeks at 60° C. | 183 | 26.91 | |

The data summarized in Examples 6 through 13 of TABLE II illustrate the increased stability of an indicator reagent composition of the present invention. For example, TABLE II summarizes the results of stress tests performed on test strips of Examples 6 and 7 incorporating an indicator reagent composition that omitted the morpholinopropanesulfonic acid (MOPS) buffer and the triisopropanolamine borate (TIB) stabilizer. The stressed test strip of Example 7 exhibited a percent reflectance of 51.93%, or a change of 28.86 percentage units from the 23.07% reflectance exhibited by the unstressed test strip of Example 6. Furthermore, the concentration of unreacted 3,3'5,5'-tetramethylbenzidine (TMB) indicator dye decreased from 201 ug/cm$^2$ (micrograms per square centimeter of test pad) in the unstressed test strip of Example 6 to 121 ug/cm$^2$ in the stressed test strip of Example 7, or an approximately 40% decrease in TMB concentration. The substantial change in percent reflectance and the decrease in TMB concentration between the stressed and unstressed test strips show that, in the absence of an amine borate, the indicator dye present in the indicator reagent composition is interacting prematurely with the hydroperoxide.

The test results summarized in TABLE II for the test strips of Examples 6 and 7 should be compared to the test results summarized for the test strips of Examples 8 and 9, wherein test strips incorporated an indicator reagent composition omitting the MOPS buffer, but including the hydrolysis-resistant TIB amine borate. The test strips of Examples 8 and 9 were subjected to the identical stress test as the test strips of Examples 6 and 7. The test results after storage at −23° C. for two weeks essentially were identical for Examples 6 and 8. However, in Example 9, wherein the test strip was stress tested by storage at 60° C., a substantial improvement in stability over the test strips of Example 7 was demonstrated. The change in percent reflectance between Example 8 (unstressed) and Example 9 (stressed) is only 6.59 percentage units, compared to the 28.86 change in percentage units between Example 6 and Example 7. Furthermore, Example 9 exhibited only a 16% decrease in concentration of the TMB indicator dye from 204 ug/cm$^2$ to 172 ug/cm$^2$. Accordingly, the test strips utilized in Examples 8 and 9, including the GPA and a second buffer, MOPS, in the indicator reagent composition (EX. 11 compared to EX. 7); and that including the TIB amine borate substantially increases the stability of the test strip (EX. 13 compared to EX. 11). In particular, the change in reflectance percentage units is only 4.30 between the unstressed test strip of Example 12 and the stressed test strip of Example 13, compared to a 25.40 change in percentage units between unstressed test strip Example 10 and stressed test strip of Example 11 absent a hydrolysis-resistant bicyclic amine borate. Furthermore, the concentration of the TMB indicator dye decreased only about 9% (from 201 ug/cm$^2$ to 183 ug/cm$^2$) in the stressed test strip of Example 13 compared to unstressed test strip of Example 12, whereas the concentration of TMB decreased by about 30% (from 202 ug/cm$^2$ to 141 ug/cm$^2$) in the stressed and unstressed test strips of Examples 11 and 12 absent an amine borate. It also has been found that a test strip incorporating the indicator reagent composition of Formulation #2 accurately detected 0.045 mg/dL of hemoglobin in a standardized test sample after storing the test strip at 50° C. for eight weeks.

Accordingly, including an amine borate compound of general structural formula (I) or (II) in an indicator reagent composition used in a dry phase test strip assay for a peroxidatively active substance stabilizes the indicator reagent composition and a more sensitive assay is achieved. Therefore, in accordance with an important feature of the present invention, the continuing and substantial problems in dry phase test strips for a peroxidatively active substance of premature interaction between an indicator dye and a hydroperoxide, and of the increase in pH of the indicator reagent composition upon exposure to environmental humidity are essentially eliminated. The discovery of an indicator reagent composition that essentially eliminates the development of a blank color, and therefore essentially eliminates the problem of a false positive assay, is an unexpected improvement in the art of dry phase test strip assays for a peroxidatively active substance, such as the assay for occult blood. In addition, the indicator reagent composition maintains an essentially constant pH during storage and exposure to environmental humidity, therefore improving assay sensitivity, especially to low concentrations of a peroxidatively active substance. Therefore, in accordance with an important feature of the present invention, more accurate and reliable assays for a peroxidatively active substance in urine and other test samples can be performed by utilizing the indicator reagent composition of the present invention.

The composition of the present invention, comprising an indicator dye, a hydroperoxide, a buffer and a bicyclic amine borate having pendant methyl groups or ethyl groups, is sufficiently stable to prevent the indicator dye from prematurely interacting with the hydroperoxide. In addition, the indicator reagent composition maintains an essentially constant test pad pH during storage and exposure to environmental humidity. The indicator reagent composition therefore undergoes a more spectacular color transition in response to the concentration of a peroxidatively active substance in a test sample. In general, an indicator reagent composition of the present invention, including an amine borate compound of general structural formula (I) or (II), demonstrates improved stability and therefore eliminates the development of a premature background color in the test pad due to an interaction between an indicator dye and a hydroperoxide; eliminates pH changes in the test pad upon exposure to environmental humidity; prevents pH changes in the test pad after contact between the test pad and the test sample; increases the useful life of test strips that are exposed to environmental humidity; does not interfere with indicator dye oxidation by a peroxidatively active substance and a hydroperoxide; and does not interfere with ascorbate resistance provided by a metal ion complex and a hydroperoxide.

Obviously, many modifications and variations of the invention as hereinbefore set forth can be made without departing from the spirit and scope thereof and therefore only such limitations should be imposed as are indicated by the appended claims.

We claim:

1. A composition capable of exhibiting a sufficient color transition upon contacting a test sample to demonstrate the presence or concentration of a peroxidatively active substance in the test sample comprising:
   (a) an indicator dye;
   (b) a hydroperoxide;
   (c) a buffer;
   (d) an amine borate compound having the formula

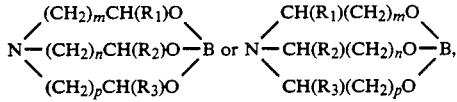

wherein $R_1$, $R_2$ and $R_3$ are, independently, a methyl group or an ethyl group, and m, n, and p are numerals ranging from one to about three; and
   (e) a suitable carrier vehicle.

2. The composition of claim 1 wherein the composition is capable of exhibiting a sufficient color transition to demonstrate the presence or concentration of one part of the peroxidatively active substance in one trillion parts of the test sample.

3. The composition of claim 1 wherein the indicator dye is present in an amount ranging from about 5 millimoles to about 60 millimoles per liter of the composition.

4. The composition of claim 1 wherein the indicator dye is a redox indicator.

5. The composition of claim 4 wherein the redox indicator is selected from the group consisting of benzidine; o-tolidine; a 3,3',5,5'-tetraalkylbenzidine, wherein the alkyl group includes from one to about six carbon atoms; o-dianisidine; 2,7-diaminofluorene; bis-(N-ethylquinol-2-one)-azine; (N-methylbenzthiazol-2-one)-(1-ethyl-3-phenyl-5-methyltriazol-2-one)-azine; and combinations thereof.

6. The composition of claim 1 wherein the indicator dye is 3,3',5,5'-tetramethylbenzidine.

7. The composition of claim 1 wherein the hydroperoxide is present in an amount ranging from about 5 millimoles to about 100 millimoles per liter of the composition.

8. The composition of claim 1 wherein the hydroperoxide is an organic hydroperoxide.

9. The composition of claim 1 wherein the hydroperoxide is selected from the group consisting of cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-t-butylisopropylbenzene hydroperoxide, 2(α-hydroperoxyisopropyl)-6-isopropylnaphthalene, tetralin hydroperoxide and combinations thereof.

10. The composition of claim 1 wherein the hydroperoxide is 1,4-diisopropylbenzene monohydroperoxide.

11. The composition of claim 1 wherein the buffer is present in an amount ranging from about 50 millimoles to about 600 millimoles per liter of the composition.

12. The composition of claim 1 wherein the buffer is selected from the group consisting of acetate; phthalate; borate; trichloroacetate; sulfosalicylate; phosphate; tartarate; citrate; succinate; maleic acid; 2,2-bis(hydroxymethyl)-2,2',2''-nitrilotriethanol; 1,4-piperazinebis(ethanesulfonic acid); 3,3-dimethylglutaric acid; 3-N-morpholinopropanesulfonic acid; malonic acid; 1,3-bis[tris(-hydroxymethyl)methylamino]propane; tris(hydroxymethyl aminomethane; tris(hydroxymethyl)aminomethane-maleic acid; tris(hydroxymethyl)aminomethanemalonic acid; 3-[N-tris(hydroxymethyl)methylamino]-2-hydroxypropanesulfonic acid; 2-[tris(hydroxymethyl)methylamino]ethanesulfonic acid; 4-morpholinoethanesulfonic acid; N-2-hdyroxyethylpiperazIne-N'-2-ethanesulfonic acid and combinations thereof.

13. The composition of claim 1 wherein the buffer is a phosphorus compound having the formula

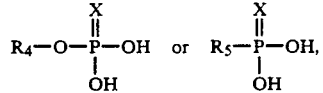

wherein $R_4$ or $R_5$ is selected from the group consisting of hydrogen, an unsubstituted or a substituted alkyl moiety including from one to about twelve carbon atoms, an unsubstituted or a substituted aromatic moiety and a residue of an aliphatic or an aromatic polyhydric compound, and wherein X is O, S or NH.

14. The composition of claim 13 wherein $R_4$ or $R_5$ of the phosphorus compound is a substituted or an unsubstituted alkyl moiety including from about five to about ten carbon atoms.

15. The composition of claim 13 wherein $R_4$ or $R_5$ of the phosphorus compound is a substituted or an unsubstituted carbocyclic or heterocyclic aromatic moiety.

16. The composition of claim 13 wherein $R_4$ or $R_5$ of the phosphorus compound is a substituted or an unsubstituted aromatic moiety selected from the group consisting of benzene, naphthalene, pyrrole, furan, pyrimidine, thiophene, pyridine, pyrazine, indole, quinoline, carbazole, purine, isoquinoline, isothiazole, and isoxazole.

17. The composition of claim 13 wherein $R_4$ or $R_5$ of the phosphorus compound is a residue of a polyhydric compound selected form the group consisting of a glycol, a triol, a polyol, a saccharide, and a hydroxyphenol.

18. The composition of claim 13 wherein $R_4$ or $R_5$ of the phosphorus compound is a residue of a polyhydric compound selected from the group consisting of ethylene glycol, propylene glycol, butylene glycol, hexanediol, glycerol, neopentyl, glycol, diethylene glycol, dipropylene glycol, triethylene glycol, cyclopentanediol, cyclohexanediol, hydrobenzoin, glucose, fructose, and sorbitol.

19. The composition of claim 13 wherein the phosphorus compound is selected from the group consisting of glyceryl-2-phosphate, phosphonic acid, phenyl dihydrogen phosphate, p-nitrophenyl dihydrogen phosphate, phosphoric acid, ethyl dihydrogen phosphate, and phenylphosphonic acid.

20. This composition of claim 1 wherein the amine borate is present in an amount ranging from about 25 millimoles to about 400 millimoles per liter of the composition.

21. The composition of claim 1 wherein the amine borate is triisopropanolamine borate.

22. The composition of claim 1 wherein the carrier vehicle, comprises water.

23. The composition of claim 22 wherein the carrier vehicle further comprises from 0% to about 90% by weight of the carrier vehicle of an organic solvent.

24. The composition of claim 1 having a pH in the range of from about 5 to about 7.

25. The composition of claim 1 further comprising a metal ion complex in an amount up to about 50 millimoles per liter of composition.

26. The composition of claim 25 wherein the metal ion complex is a ferric ion complex.

27. The composition of claim 26 wherein the ferric ion complex is selected from the group consisting of ferric ion complexes of N-(2-hydroxyethyl)ethylenediaminetriacetic acid, ethylenediaminetetraacetic acid, cyclohexylenediaminetetraacetic acid, nitrilotriacetic acid, iminodiacetic acid, ethylenediaminediacetic dipropionic acid, hydroxyethyliminodiacetic acid, diethylenetriaminepentaacetic acid, ethylenebis(oxyethylenenitrilo)tetraacetic acid, N-(2-acetamino)imonodiacetic acid, citric acid, gluconic acid, a glucoheptonate, bissalicylaldehydeethylenediminato, triethylenepyridine amine and combinations thereof.

28. The composition of claim 25 wherein the metal ion complex is a ferric ion complex of N-(2-hydroxyethyl)ethylenediaminetriacetic acid, ethylenediaminetetraacetic acid or a combination thereof.

29. The composition of claim 1 comprising from about 20 millimoles to about 40 millimoles of the indicator dye 3,3',5,5'-tetramethylbenzidine per liter of the composition; from about 25 millimoles to about 75 millimoles of the hydroperoxide 1,4-diisopropylbenzene monohydroperoxide per liter of the composition; from about 50 millimoles to about 300 millimoles of the amine borate triisopropanolamine borate per liter of the composition; and from about 100 millimoles to about 400 millimoles of the buffer glyceryl-2-phosphate per liter of the composition.

30. The composition of claim 29 further comprising from about 1 millimole to about 25 millimoles of the metal ion complex ferric N-(2-hydroxyethyl)ethylenediaminetriacetic acid per liter of the composition.

31. A method of determining the presence or concentration of a peroxidatively active substance in a test sample comprising:
(a) contacting the test sample with a composition comprising an indicator dye, a hydroperoxide, a buffer, an amine borate compound having the formula

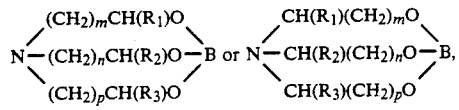

wherein $R_1$, $R_2$ and $R_3$ are, independently, a methyl group or an ethyl group, and m, n and p are numerals ranging from one to about three, and a suitable carrier vehicle; and
(b) determining the presence or concentration of the peroxidatively active substance in the test sample from the intensity or degree of a color change of the composition.

32. The method of claim 31 wherein the intensity or degree of a color change is determined visually or instrumentally.

33. The method of claim 31 wherein the presence or concentration of the peroxidatively active substance is determined by a dry phase assay.

34. The method of claim 31 wherein the test sample is a biological fluid.

35. The method of claim 31 wherein the biological fluid is urine, feces or vomit.

36. The method of claim 31 wherein the peroxidately active substance is selected from the group consisting of hemoglobin, a hemoglobin derivative, an erythrocyte, myoglobin and combinations thereof.

37. The method of claim 31 wherein the presence or concentration of the peroxidatively active substance is determined at a concentration as low as one part of the peroxidatively active substance per one trillion parts of the test sample.

38. The method of claim 31 wherein the indicator dye is a redox indicator and is present in an amount ranging from about 5 millimoles to about 60 millimoles per liter of the composition.

39. The method of claim 31 wherein the hydroperoxide is an organic hydroperoxide and is present in an amount ranging from about 5 millimoles to about 100 millimoles per liter of the composition.

40. The method of claim 31 wherein the buffer is present in an amount ranging from about 50 millimoles to about 600 millimoles per liter of the composition.

41. The method of claim 40 wherein the buffer is a phosphorus compound having the formula

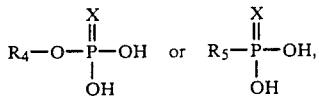

wherein $R_4$ or $R_5$ is selected from the group consisting of hydrogen, an unsubstituted or a substituted alkyl moiety including from one to about twelve carbon atoms, an unsubstituted or a substituted aromatic moiety and a residue of an aliphatic or an aromatic polyhydric compound, and wherein X is O, S or NH.

42. The method of claim 31 wherein the amine borate is present in an amount ranging from about 25 millimoles to about 400 millimoles per liter of the composition.

43. The method of claim 31 wherein the amine borate is triisopropanolamine borate.

44. The method of claim 31 wherein the carrier vehicle comprises water.

45. The method of claim 31 wherein the composition has a pH in the range of from about 5 to about 7.

46. A method of determining the presence or concentration of occult blood in a biological fluid comprising:
 (a) contacting a test sample of the biological fluid with a composition comprising an indicator dye, a hydroperoxide, a buffer, an amine borate compound having the formula

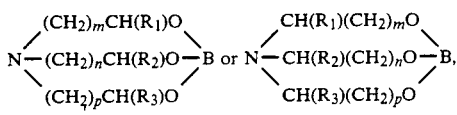

wherein $R_1$, $R_2$ and $R_3$ are, independently, a methyl group or an ethyl group, and m, n and p are numerals ranging from one to about three, and a suitable carrier vehicle; and
 (b) determining the presence or concentration of the occult blood in the biological fluid from the intensity or degree of a color change of the composition.

47. A method of determining the presence or concentration of a peroxidatively active compound in a liquid sample comprising:
 (a) contacting the liquid sample with an analyte detection device comprising a reagent test pad including a composition comprising an indicator dye, a hydroperoxide, a buffer, an amine borate compound having the formula

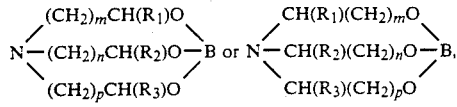

wherein $R_1$, $R_2$ and $R_3$ are, independently, a methyl group or an ethyl group, and m, n and p are numerals ranging from one to about three, and a suitable carrier vehicle; and
 (b) examining the analyte detection device for a color transition in response to the peroxidatively active substance content present in the liquid sample.

48. The method of claim 47 wherein the peroxidatively active substance is occult blood and the liquid sample is a biological fluid.

49. The method of claim 48 wherein the biological fluid is urine.

50. An analyte detection device to determine the presence or concentration of a peroxidatively active substance in a liquid test sample comprising:
 a support strip;
 a reagent test pad; and
 a composition incorporated into the reagent test pad, said composition comprising
 (a) an indicator dye;
 (b) a hydroperoxide;
 (c) a buffer;
 (d) an amine borate compound having the formula

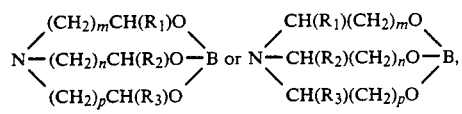

wherein $R_1$, $R_2$ and $R_3$ are, independently, a methyl group or an ethyl group, and m, n and p are numerals ranging from one to about three; and
 (e) a suitable carrier vehicle.

* * * * *